(12) United States Patent
Roy et al.

(10) Patent No.: US 11,238,243 B2
(45) Date of Patent: Feb. 1, 2022

(54) EXTRACTING JOINT TOPIC-SENTIMENT MODELS FROM TEXT INPUTS

(71) Applicant: Optum Technology, Inc., Eden Prairie, MN (US)

(72) Inventors: Suman Roy, Bangalore (IN); Malladi Vijay Varma, Hyderabad (IN); Siddhartha Asthana, Ghaziabad (IN); Madhvi Gupta, New Delhi (IN); Ashish Chaturvedi, Noida (IN)

(73) Assignee: Optum Technology, Inc., Eden Prairie, MN (US)

( * ) Notice: Subject to any disclaimer, the term of this patent is extended or adjusted under 35 U.S.C. 154(b) by 312 days.

(21) Appl. No.: 16/585,201

(22) Filed: Sep. 27, 2019

(65) Prior Publication Data

US 2021/0097145 A1 Apr. 1, 2021

(51) Int. Cl.
*G06F 40/30* (2020.01)
*G06F 40/56* (2020.01)
(Continued)

(52) U.S. Cl.
CPC ............ *G06F 40/56* (2020.01); *G06F 40/279* (2020.01); *G06F 40/284* (2020.01);
(Continued)

(58) Field of Classification Search
CPC .......... G06F 40/00; G06F 16/80; G06F 16/90; G06F 40/284; G06F 40/295; G06F 40/279; G06F 40/30; G06F 40/42
See application file for complete search history.

(56) References Cited

U.S. PATENT DOCUMENTS 7,788,264 B2 8/2010 Zhu et al.
8,234,274 B2 7/2012 Guo et al.
(Continued)

FOREIGN PATENT DOCUMENTS

| CN | 104199829 A | 12/2014 |
| CN | 108681557 A | 10/2018 |
| CN | 110390014 A | 10/2019 |

OTHER PUBLICATIONS

"Deeply Moving: Deep Learning For Sentiment Analysis," (6 pages), [article], [online], [Retrieved from the Internet Dec. 18, 2019] <https://nlp.stanford.edu/sentiment/>.
(Continued)

*Primary Examiner* — Sanchita Roy
(74) *Attorney, Agent, or Firm* — Alston & Bird LLP

(57) ABSTRACT

There is a need for solutions for more effective and efficient natural language processing systems for short texts. This need can be addressed, for example, by a system configured to obtain an initial term-topic correlation data object for a plurality of digital documents, obtain a user-defined term-topic correlation data object for the plurality of digital documents, generate a refined term-topic correlation data object and a refined document-sentiment correlation data object for the plurality of digital documents based at least in part on the initial term-topic correlation data object and the user-defined term-topic correlation data object, obtain a user-defined document-topic correlation data object for the plurality of digital documents, and generate a refined document-topic correlation object for the plurality of digital documents based at least in part on the refined term-topic correlation data object and the user-defined document-topic correlation data object.

20 Claims, 9 Drawing Sheets

(51) Int. Cl.

| | |
|---|---|
| *G06K 9/00* | (2006.01) |
| *G16H 15/00* | (2018.01) |
| *G06F 40/42* | (2020.01) |
| *G06F 40/279* | (2020.01) |
| *G06F 40/284* | (2020.01) |
| *G06F 40/295* | (2020.01) |

(52) U.S. Cl.
CPC ............ *G06F 40/295* (2020.01); *G06F 40/30* (2020.01); *G06F 40/42* (2020.01); *G06K 9/00469* (2013.01); *G16H 15/00* (2018.01)

(56) References Cited

U.S. PATENT DOCUMENTS

| | | |
|---|---|---|
| 8,356,086 B2 | 1/2013 | Liu et al. |
| 8,515,879 B2 | 8/2013 | Huh et al. |
| 8,682,649 B2 | 3/2014 | Bellegarda |
| 8,719,302 B2 | 5/2014 | Bailey et al. |
| 9,424,299 B2 | 8/2016 | Bufe et al. |
| 9,501,525 B2 | 11/2016 | Barker et al. |
| 10,007,716 B2 | 6/2018 | Tee |
| 10,013,480 B2 | 7/2018 | Aiello et al. |
| 10,037,320 B2 | 7/2018 | Amin et al. |
| 10,055,479 B2 | 8/2018 | Clinchant et al. |
| 10,083,176 B1 | 9/2018 | Desai et al. |
| 10,216,724 B2 | 2/2019 | Sinha et al. |
| 2014/0280361 A1 | 9/2014 | Aliferis et al. |
| 2015/0052098 A1 | 2/2015 | Kveton et al. |
| 2017/0046601 A1 | 2/2017 | Chang et al. |
| 2017/0116204 A1 | 4/2017 | Davaleu et al. |
| 2018/0165554 A1 | 6/2018 | Zhang et al. |
| 2018/0225372 A1 | 8/2018 | Lecue et al. |
| 2018/0357302 A1 | 12/2018 | Oi et al. |

OTHER PUBLICATIONS

"Sentiment Analysis," General Architecture For Text Engineering, (2 pages), [article], [online], [Retrieved from the Internet Dec. 18, 2019] <https://gate.ac.uk/applications/sentiment.html>.

"Sentiment Analysis," OpenText, (6 pages), [article], [online], [Retrieved from the Internet Dec. 18, 2019] <https://www.opentext.com/products-and-solutions/products/discovery/information-access-platform/sentiment-analysis>.

"Tone Analyzer," IBM Watson, (10 pages), [online], [Retrieved from the Internet Dec. 19, 2019] <https://www.ibm.com/watson/services/tone-analyzer/>.

26. W. Xu, X. Liu, and Y. Gong. Document Clustering Based On Non-Negative Matrix Factorization, In Proceedings of the 26th Annual International ACM SIGIR Conference on Research and Development in Information Retrieval, SIGIR '03, pp. 267-273, Jul. 28, 2003. ACM.

Alshari, Eissa et al. "Improvement of Sentiment Analysis Based on Clustering of Word2Vec Features," In 28th International Workshop on Database and Expert Systems Applications (DEXA), Aug. 29, 2017, pp. 123-126. IEEE.

Arbelaiiz, Olatz et al. "An Extensive Comparative Study of Cluster Validity Indices," Pattern Recognition, vol. 46, No. 1, (2013), pp. 243-256.

Bagheri, Ayoub et al. "ADM-LDA: An Aspect Detection Model Based on Topic Modelling Using the Structure of Review Sentences," Journal of Information Science 2014, vol. 40, Issue 5, pp. 621-636.

Blei, David M. et al. "Latent Dirichlet Allocation," Journal of Machine Learning Research, vol. 3, (2003), pp. 993-1022.

Boyd-Graber, Jordan et al. "Holistic Sentiment Analysis Across Languages: Multilingual Supervised Latent Dirichlet Allocation," Proceedings of the 2010 Conference on Empirical Methods in Natural Language Processing, Oct. 9, 2010, pp. 45-55.

Ding, Chris et al. "Orthogonal Non-Negative Matrix Tri-Factorizations for Clustering," In Proceedings of the Twelfth ACM SIGKDD International Conference on Knowledge Discovery and Data Mining, Aug. 20, 2006, pp. 126-135.

Griffiths, Griffiths and M. Steyvers. Finding scientific topics. Proceedings of the National Academy of Sciences, Apr. 6, 2004, vol. 101, Suppl. 1, pp. 5228-5235.

Hb, Barathi Ganesh et al. "Distributional Semantic Representation in Health Care Text Classification," 2016, (4 pages).

He, Zhaoshui et al. "Symmetric Nonnegative Matrix Factorization: Algorithms and Applications to Probabilistic Clustering" IEEE Transactions on Neural Networks, vol. 22, No. 12, Dec. 2011, pp. 2117-2131.

Hofmann, Thomas. "Probabilistic Latent Semantic Indexing," In SIGIR Forum, (1999), pp. 50-57, ACM.

Hu, Xia et al. "Unsupervised Sentiment Analysis With Emotional Signals," In Proceedings of the 22nd International Conference on World Wide Web May 13, 2013, pp. 607-618. ACM.

Keiningham, Timothy L et al. "A Longitudinal Examination Of Net Promoter and Firm Revenue Growth," Journal of Marketing, vol. 71, No. 3, Jul. 2007, pp. 39-51.

Kim, Soo-Min et al. "Determining The Sentiment of Opinions," In Proceedings of the 20th International Conference on Computational Linguistics Aug. 23, 2004, (7 pages), Association for Computational Linguistics.

Kuang, Da et al. "Nonnegative Matrix Factorization for Interactive Topic Modeling and Document Clustering," Springer International publishing Switzerland 2015, pp. 215-243. DOI: 10.1007/978-3-319-09259-1_7.

Lee, Daniel D. et al. "Algorithms For Non-Negative Matrix Factorization," In Advances in Neural Information Processing Systems 13, pp. 556-562, MIT Press, 2001. T.K. Leen, T.G. Dietterick, and V. Tresp, Editors.

Li, Tao et al. "A Non-Negative Matrix Tri-Factorization Approach To Sentiment Classification With Lexical Prior Knowledge." In Proceedings of the 47th Annual Meeting of the ACL and the 4th International Joint Conference on Natural Language Processing of the AFNLP, pp. 244-252, Aug. 2, 2009, Suntec, Singapore.

Li, Tao et al. "Knowledge Transformation From Word Space to Document Space," In Proceedings of the 31st Annual International ACM SIGIR'08, pp. 187-194, Jul. 20, 2008, Singapore.

Lin, Chenghua et al. "Joint Sentiment Topic Model For Sentiment Analysis," In Proceedings of the 18th ACM Conference on Information and Knowledge Management, CIKM '09, pp. 375-384, Nov. 2, 2009. ACM.

Liu, Bing et al. "Opinion Observer: Analyzing and Comparing Opinions on the Web," In Proceedings of the 14th International Conference on World Wide Web, WWW'05, pp. 342-351, May 10, 2005, Chiba, Japan.

Mei, Qiaozhu et al. "Automatic Labeling of Multinomial Topic Models," In Proceedings of the 13th ACM SIGKDD International Conference on Knowledge Discovery and Data Mining, pp. 490-499, Aug. 12, 2007, San Jose, California.

Mei, Qiaozhu et al. "Topic Sentiment Mixture: Modeling Facets and Opinions in Weblogs," In Proceedings of the 16th International Conference on World Wide Web, WWW'07, pp. 171-180, May 8, 2007, Banff, Alberta, Canada.

Mikolov, Tomas et al. "Efficient Estimation of Word Representations in Vector Space," pp. 1-12, arXiv 1301.3781v3 [cs.CL], Sep. 7, 2013.

O'Hare, Neil et al. "Topic-Dependent Sentiment Analysis of Financial Blogs," In Proceedings of the 1st International CIKM Workshop on Topic-Sentiment Analysis for Mass Opinion Measurement, Nov. 6, 2009, pp. 9-16, Hong Kong, China. ACM.

Pang, Bo et al. "Opinion Mining and Sentiment Analysis," Foundations and Trends In Information Retrieval, vol. 2, No. 1-2, pp. 1-135, (2008).

Pang, Bo et al. "Thumbs Up? Sentiment Classification Using Machine Learning Techniques," In Proceedings of the 2002 Conference on Empirical Methods in Natural Language Processing (EMNLP), arXiv:cs/0205070v1 [cs.CL], May 28, 2002.

Poddar, Lahari et al. "Author-Aware Aspect Topic Sentiment Model to Retrieve Supporting Opinions From Reviews," In Proceedings of

(56) References Cited

OTHER PUBLICATIONS the 2017 Conference on Empirical Methods in Natural Language Processing, EMNLP'17, pp. 472-481, Sep. 7, 2017, Copenhagen, Denmark.
Rahman, Md Mustafizur et al. "Hidden Topic Sentiment Model," In Proceedings of the 25th International Conference on World Wide Web, WWW '16, pp. 155-165, Apr. 11, 2016, Montreal, Quebec, Canada.
Titov, Ivan et al. "A Joint Model of Text and Aspect Ratings For Sentiment Summarization," In Proceedings of ACL-08: HLT, pp. 308-316, Jun. 2008, Association For Computational Linguistics.
Turney, Peter D. "Thumbs Up or Thumbs Down? Semantic Orientation Applied to Unsupervised Classification of Reviews," In Proceedings of the 40th Annual Meeting of the Association for Computational Linguistics (ACL)'04, pp. 417-424, Jul. 6, 2002.
Waggoner, Alexander A. "Triple Non-Negative Matrix Factorization Technique for Sentiment Analysis and Topic Modeling," (2017), CMC Senior Theses.1550, Claremont McKenna College, (25 pages). [Retrieved from the Internet Dec. 18, 2019] <https://scholarship.claremont.edU/cmc_theses/1550/>.
Yan, Xiaohui et al. "Learning Topics in Short Texts by Non-Negative Matrix Factorization on Term Correlation Matrix," In Proceedings of the 13th SIAM International Conference on Data Mining, May 2, 2013, pp. 749-757, Society For Industrial and Applied Mathematics.
Zhao, Jun et al. "Adding Redundant Features For CRFs-Based Sentence Sentiment Classification," In Proceedings of the 2008 Conference on Empirical Methods in Natural Language Processing, EMNLP '08, pp. 117-126, Oct. 2008, Association for Computational Linguistics, Honolulu, Hawaii.
"DEMO: Online Latent Dirichelt Allocation," (Article, Online), (1 page). [Retrieved online Jun. 10, 2021] <https://www.logos.t.u-tokyo.ac.jp/~eriguchi/demo/olda/>.
Canini, Kevin R. et al. "Online Inference of Topics With Latent Dirichlet Allocation," In Artificial Intelligence and Statistics, Apr. 15, 2009, pp. 65-72, Proceedings of Machine Learning Research.
Flinchbaugh, Anne et al. "ReelTalk: An Interactive Sentiment Analysis Application," Silo. Tips, Apr. 17, 2018, (6 pages). https://silo.tips/download/reeltalk-an-interactive-sentiment-analysis-application#.
Gadelrab, Fatma S et al. "Novel Semantic Tagging Detection Algorithms Based Non-Negative Matrix Factorization," SN Applied Sciences, vol. 2, No. 54 (2020), pp. 1-18, published online: Dec. 9, 2019, Switzerland. https://doi.org/10.1007/s42452-019-1836-y.
Hu, Yuening et al. "Interactive Topic Modeling," Machine Learning, Jun. 1, 2014, vol. 95, No. 3, pp. 423-469.
Suh, Sangho et al. "Localized User-Driven Topic Discovery via Boosted Ensemble of Nonnegative Matrix Factorization," Knowledge and Information Systems, vol. 56, No. 3, (29 pages), Sep. 2018, published online Jan. 8, 2018. DOI: 10.1007/s10115-017-1147-9.
"Sklearn decompisition.LatentDirichletAllocation," (5 pages) [Online]. [Retrieved from the Internet Jan. 1, 2021] <https://scikit-learn.org/stable/modules/generated/sklearn.decomposition.LatentDirichletAllocation.html>.
"Topic Modelling For Humans," GENSIM, (6 pages), [online] [Retrieved from the Internet Dec. 30, 2020] <https://radimrehurek.com/gensim/>.
Alsumait, Loulwah et al. "On-line LDA: Adaptive Topic Models for Mining Text Streams With Applications to Topic Detection and Tracking," In 2008 Eighth IEEE International Conference on Data Mining, Dec. 15, 2008, (pp. 3-12). IEEE.
Blei, David M et al. "Dynamic Topic models," In Proceedings of the 23rd International Conference on Machine Learning, Jun. 25, 2006. pp. 113-120.
Bottou, Leon. "Stochastic Learning," In O. Bousquet et al. (EDS) Advanced Lectures on Machine Learning 2003. Lecture Notes in Computer Science, vol. 3176, (2004), pp. 146-168. Springer, Berlin, Heidelberg. DOI:10.1007/978-3-540-28650-9_7.

Bucak, Serhat S et al. "Incremental Subspace Learning via Non-Negative Matrix Factorization," Pattern Recognition, vol. 42, Issue 5, (2009), pp. 788-797. ISSN 0031-3203. DOI: 10.1016/j.patcog.2008.09.002.
Cao, Bin et al. "Detect and Track Latent Factors with Online Nonnegative Matrix Factorization," In Proceedings of IJCAI, vol. 7, Jan. 6, 2007, pp. 2689-2694.
Chen, Guan-Bin et al. "Word Co-Occurrence Augmented Topic Model in Short Text," Computational Linguistics and Chinese Language Processing, vol. 20, No. 2, Dec. 2015, pp. 45-64.
Choo, Jaegul et al. "Utopian: User-Driven Topic Modeling Based on Interactive Nonnegative Matrix Factorization." IEEE Transactions on Visualization and Computer Graphics, vol. 19, No. 12, Dec. 13, pp. 1992-2001.
Guan, Naiyang et al. "Online Nonnegative Matrix Factorization With Robust Stochastic Approximation," IEEE TransACTIONS on Neural Networks and Learning Systems, vol. 23, No. 7, Jul. 2012, pp. 1087-1099.
Hoffman, Matthew D. et al. "Online Learning For Latent Dirichlet Allocation," In: Advances in Neural Information Processing Systems, vol. 23, (9 pages), 24th Annual Conference on Neural Information Processing Systems, Proceedings of a Meeting Held Dec. 6-9, 2010.
Iwata, Tomoharu et al. "Online Multiscale Dynamic Topic Models," In Proceedings of the 16th ACM SIGKDD International Conference on Knowledge Discovery and Data Mining, (2010), (10 pages).
Kim, Hyunsoo et al. "Non-Negative Matrix Factorization Based on Alternating Non-Negativity Constrained Least Squares and Active Set Method," SIAM Journal on Matrix Analysis and Applications, vol. 30, No. 2, (2008), (16 pages).
Kim, Jingu et al. "Algorithms For Non-Negative Matrix and Tensor Factorizations: A Unified View Based on Block Coordinate Descent Framework," Journal of Global Optimization, No. 58, No. 2, (2014), pp. 285-319. DOI 10.1007/s10898-013-0035-4.
Kim, Jingu et al. "Fast Non-Negative Matrix Factorization: An Active-Set-Like Method and Comparisons," SIAM Journal on Scientific Computing, vol. 33, No. 6, (2011), (21 pages).
Leskovec, Jure et al. "Mining of Massive Datasets," 2nd Edition, Tanagra Data Mining, Cambridge University Press (2014), pp. 1-16.
Li, Chenliang et al. "Topic Modeling For Short Texts With Auxiliary Word Embedding," In Proceedings of the 39th International ACM SIGIR Conference on Research and Development in Information Retrieval, Jul. 7, 2016, pp. 165-174.
Lin, Chih-Jen. "Projected Gradient Methods For Non-Negative Matrix Factorization," Neural Computation, vol. 19, No. 10, Oct. 2007, (27 pages).
Nugroho, Robertus et al. "Deriving Topics in Twitter by Exploiting Tweet Interactions," In 2015 IEEE International Congress on Big Data, Jun. 27-Jul. 2, 2015, pp. 87-94. New York City, NY, USA. DOI: 10.1109/BigDataCongress.2015.22.
Qiang, Jipeng et al. "Topic Modeling Over Short Texts By Incorporating Word Embeddings," arXiv: 1609.08496v1 [cs.CL] Sep. 27, 2016, (10 pages). DOI: 10.1145/1235. ACM ISBN: 978-1-4503-2138-9.
Quan, Xiaojun et al. "Short and Sparse Text Topic Modeling via Self-Aggregation, " In Proceedings of the 24th International Conference on Artificial Intelligence, IJCAI 2015, AAAI Press (2015), 2270-2276.
Röder, Michael et al. "Exploring the Space of Topic Coherence Measures," In Proceedings of the Eighth ACM International Conference on Web Search and Data Mining, WSDM 2015, ACM (2015), pp. 399-408.
Roy, Suman et al. "A NMF-Based Learning of Topics and Clusters for IT Maintenance Tickets Aided by Heuristic," In Information Systems in the Big Data Era—CAiSE Forum 2018, Proceedings, (2018), LNBIP 317, pp. 209-217. DOI: 10.1007/978-3-319-92901-9_18.
Sasaki, Kentaro et al. "Online Topic Model for Twitter Considering Dynamics of User Interests and Topic Trends," In Proceedings of the 2014 Conference on Empirical Methods in Natural Language Processing (EMNLP), Oct. 2014, pp. 1977-1985.

(56) References Cited

OTHER PUBLICATIONS

Shi, Tian et al. "Short-Text Topic Modeling via Non-Negative Matrix Factorization Enriched With Local Word-Context Correlations," In Proceedings of the 2018 World Wide Web Conference, Apr. 10, 2018, pp. 1105-1114.

Tibshirani, Robert, "Regression Shrinkage and Selection via the Lasso," Journal of the Royal Statistical Society, Series B (Methodological), vol. 58, Issue 1, (1996), pp. 267-288.

Wang, Fei et al. "Efficient Document Clustering via Online Nonnegative Matrix Factorizations," In Eleventh SIAM International Conference on Data Mining, Society for Industrial and Applied Mathematics, (SDM), (2011), pp. 908-919.

Wang, Fei et al. "Efficient Nonnegative Matrix Factorization With Random Projections," In Proceedings of the 2010 Society for Industrial and Applied Mathematics (SIAM) International Conference on Data Mining, Apr. 29, 2010, pp. 281-292.

Wang, Fei et al. "Two Heads Better Than One: Metric+Active Learning and Its Applications for IT Service Classification," The Ninth IEEE International Conference on Data Mining, (2009), pp. 1022-1027.

Wang, Xuerui et al. "Topics Over Time: A Non-Markov Continuous-Time Model of Topical Trends," In Proceedings of the 12th ACM SIGKDD International Conference on Knowledge Discovery and Data Mining, Aug. 20, 2006, pp. 424-433.

Xun, Guangxu et al. "Topic Discovery For Short Texts Using Word Embeddings," In IEEE 16th International Conference on Data Mining, ICDM'16, (2016), pp. 1299-1304. DOI: 10.1109/ICDM.2016.33.

Yan, Xiaohui et al. "Learning Topics in Short Texts by Non-Negative Matrix Factorization on Term Correlation Matrix," In Proceedings of the 2013 Society for Industrial and Applied Mathematics International Conference on Data Mining SIAM, May 2, 2013, pp. 749-757. [Retrieved from the Internet Jan. 1, 2021] <https://pdfs.semanticscholar.org/b5d0/36429877568a648389531e323ea0983a5148.pdf?ga=2.157248957.700061297.1609543144-615072438.1609543144>.

Zhou, Guoxu et al. "Online Blind Source Separation Using Incremental Non-Negative Matrix Factorization With Volume Constraint," IEEE Transactions on Neural Networks, Apr. 2011, vol. 22, No. 4, pp. 550-560.

Zuo Yuan et al. "Topic Modeling of Short Texts: A Pseudo-Document View," In Proceedings of the 22nd ACM SIGKDD International Conference on Knowledge Discovery and Data Mining, Aug. 13, 2016, pp. 2105-2114.

Lau, Jey Han et al. "Automatic Labelling of Topic Models," Proceedings of the 49th Annual Meeting of the Association for Computational Linguistics, pp. 1536-1545, Jun. 19-24, 2011.

EXTRACTING JOINT TOPIC-SENTIMENT MODELS FROM TEXT INPUTS

BACKGROUND

Many existing natural language processing (NLP) systems face technical challenges in accurately and efficiently detecting reliable properties for NLP input data. Through ingenuity and innovation, various embodiments of the present invention make substantial improvements in the efficiency and reliability of NLP systems, including by improving capabilities of NLP systems to address technical challenges in accurately and efficiently detecting reliable properties for NLP input data.

BRIEF SUMMARY

In general, embodiments of the present invention provide methods, apparatus, systems, computing devices, computing entities, and/or the like for user-defined NLP. Certain embodiments utilize systems, methods, and computer program products that enable NLP by detecting joint sentiment-topic models for NLP input data based at least in part on user topic-sentiment definitions.

In accordance with one aspect, a method is provided. In one embodiment, the method comprises obtaining, by one or more processors, an initial term-topic correlation data object for a plurality of digital documents, wherein: (1) the initial term-topic correlation data object comprises a plurality of initial term-topic correlation indicators, and (2) the plurality of initial term-topic correlation indicators describe initial term-topic relationships between a plurality of terms and a plurality of initial topics; obtaining, by the one or more processors, a user-defined term-topic correlation data object for the plurality of digital documents, wherein: (1) the user-defined term-topic correlation data object comprises a plurality of user-defined term-topic correlation indicators, and (2) the plurality of user-defined term-topic correlation indicators describe user-defined term-topic relationships between the plurality of terms and one or more user-defined topics; generating, by the one or more processors, a refined term-topic correlation data object and a refined document-sentiment correlation data object for the plurality of digital documents based at least in part on the initial term-topic correlation data object and the user-defined term-topic correlation data object, wherein: (1) the refined term-topic correlation data object comprises a plurality of refined term-topic correlation indicators, (2) the plurality of refined term-topic correlation indicators describe refined term-topic relationships between the plurality of terms and the one or more user-defined topics, and (3) the refined document-sentiment correlation data object comprises a refined sentiment value for each digital document of the plurality of digital documents; obtaining, by the one or more processors, a user-defined document-topic correlation data object for the plurality of digital documents, wherein: (1) the user-defined document-topic correlation data object comprises a plurality of user-defined document-topic correlation indicators, and (2) the plurality of user-defined term-topic correlation indicators describe user-defined relationships between the plurality of digital documents and the one or more user-defined topics; and generating, by the one or more processors, a refined document-topic correlation object for the plurality of digital documents based at least in part on the refined term-topic correlation data object and the user-defined document-topic correlation data object, wherein: (1) the refined document-topic correlation data object comprises a plurality of refined document-topic correlation objects, and (2) the plurality of refined document-topic correlation indicators describe user-defined document-topic relationships between the plurality of digital documents and the one or more user-defined topics.

In accordance with another aspect, a computer program product is provided. The computer program product may comprise at least one computer-readable storage medium having computer-readable program code portions stored therein, the computer-readable program code portions comprising executable portions configured to obtain, by one or more processors, an initial term-topic correlation data object for a plurality of digital documents, wherein: (1) the initial term-topic correlation data object comprises a plurality of initial term-topic correlation indicators, and (2) the plurality of initial term-topic correlation indicators describe initial term-topic relationships between a plurality of terms and a plurality of initial topics; obtain, by the one or more processors, a user-defined term-topic correlation data object for the plurality of digital documents, wherein: (1) the user-defined term-topic correlation data object comprises a plurality of user-defined term-topic correlation indicators, and (2) the plurality of user-defined term-topic correlation indicators describe user-defined term-topic relationships between the plurality of terms and one or more user-defined topics; generate, by the one or more processors, a refined term-topic correlation data object and a refined document-sentiment correlation data object for the plurality of digital documents based at least in part on the initial term-topic correlation data object and the user-defined term-topic correlation data object, wherein: (1) the refined term-topic correlation data object comprises a plurality of refined term-topic correlation indicators, (2) the plurality of refined term-topic correlation indicators describe refined term-topic relationships between the plurality of terms and the one or more user-defined topics, and (3) the refined document-sentiment correlation data object comprises a refined sentiment value for each digital document of the plurality of digital documents; obtain, by the one or more processors, a user-defined document-topic correlation data object for the plurality of digital documents, wherein: (1) the user-defined document-topic correlation data object comprises a plurality of user-defined document-topic correlation indicators, and (2) the plurality of user-defined term-topic correlation indicators describe user-defined relationships between the plurality of digital documents and the one or more user-defined topics; and generate, by the one or more processors, a refined document-topic correlation object for the plurality of digital documents based at least in part on the refined term-topic correlation data object and the user-defined document-topic correlation data object, wherein: (1) the refined document-topic correlation data object comprises a plurality of refined document-topic correlation objects, and (2) the plurality of refined document-topic correlation indicators describe user-defined document-topic relationships between the plurality of digital documents and the one or more user-defined topics.

In accordance with yet another aspect, an apparatus comprising at least one processor and at least one memory including computer program code is provided. In one embodiment, the at least one memory and the computer program code may be configured to, with the processor, cause the apparatus to obtain, by one or more processors, an initial term-topic correlation data object for a plurality of digital documents, wherein: (1) the initial term-topic correlation data object comprises a plurality of initial term-topic correlation indicators, and (2) the plurality of initial term-topic correlation indicators describe initial term-topic relationships between a plurality of terms and a plurality of initial topics; obtain, by the one or more processors, a user-defined term-topic correlation data object for the plurality of digital documents, wherein: (1) the user-defined term-topic correlation data object comprises a plurality of user-defined term-topic correlation indicators, and (2) the plurality of user-defined term-topic correlation indicators describe user-defined term-topic relationships between the plurality of terms and one or more user-defined topics; generate, by the one or more processors, a refined term-topic correlation data object and a refined document-sentiment correlation data object for the plurality of digital documents based at least in part on the initial term-topic correlation data object and the user-defined term-topic correlation data object, wherein: (1) the refined term-topic correlation data object comprises a plurality of refined term-topic correlation indicators, (2) the plurality of refined term-topic correlation indicators describe refined term-topic relationships between the plurality of terms and the one or more user-defined topics, and (3) the refined document-sentiment correlation data object comprises a refined sentiment value for each digital document of the plurality of digital documents; obtain, by the one or more processors, a user-defined document-topic correlation data object for the plurality of digital documents, wherein: (1) the user-defined document-topic correlation data object comprises a plurality of user-defined document-topic correlation indicators, and (2) the plurality of user-defined term-topic correlation indicators describe user-defined relationships between the plurality of digital documents and the one or more user-defined topics; and generate, by the one or more processors, a refined document-topic correlation object for the plurality of digital documents based at least in part on the refined term-topic correlation data object and the user-defined document-topic correlation data object, wherein: (1) the refined document-topic correlation data object comprises a plurality of refined document-topic correlation objects, and (2) the plurality of refined document-topic correlation indicators describe user-defined document-topic relationships

BRIEF DESCRIPTION OF THE DRAWINGS

Figure 1:
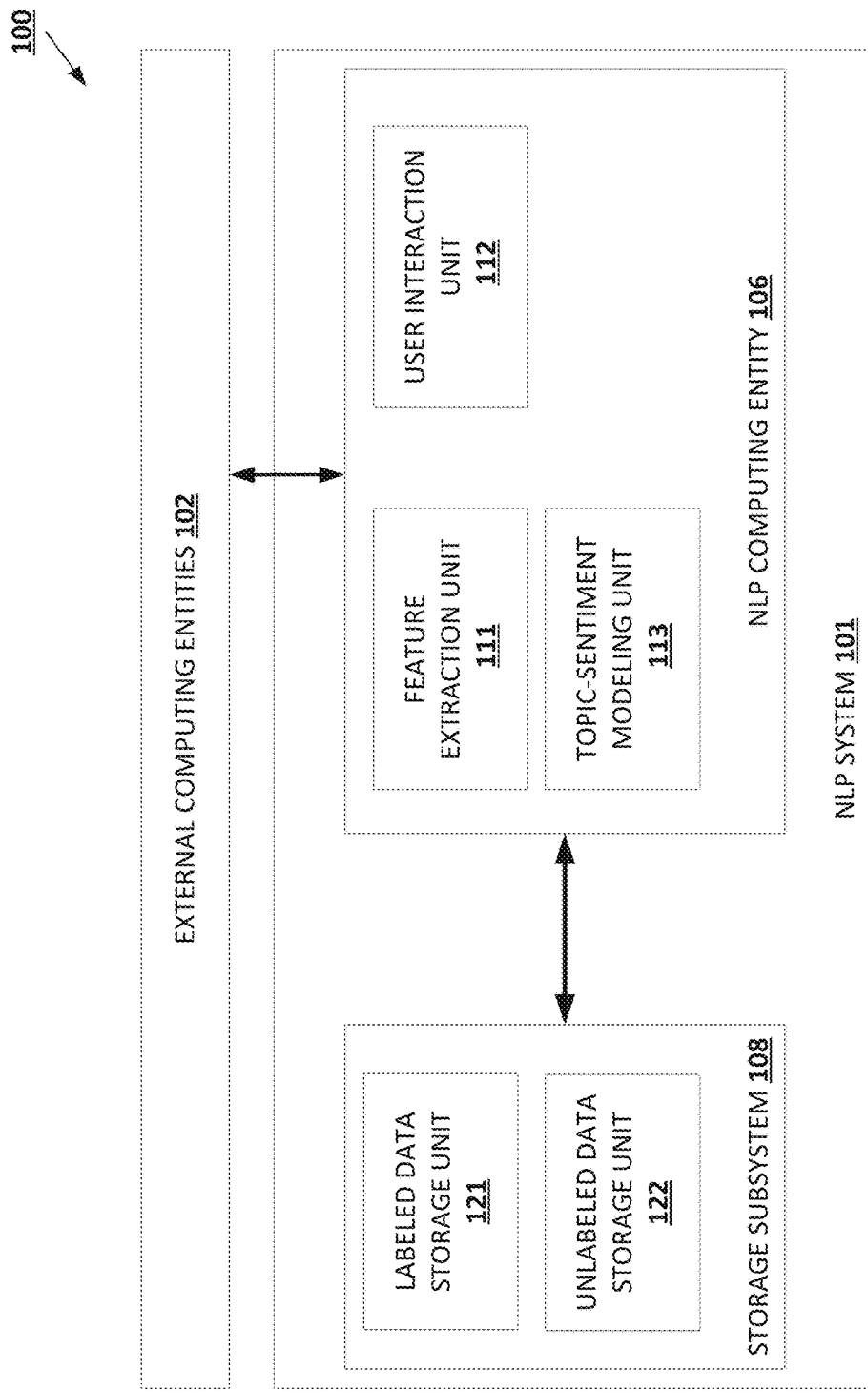

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
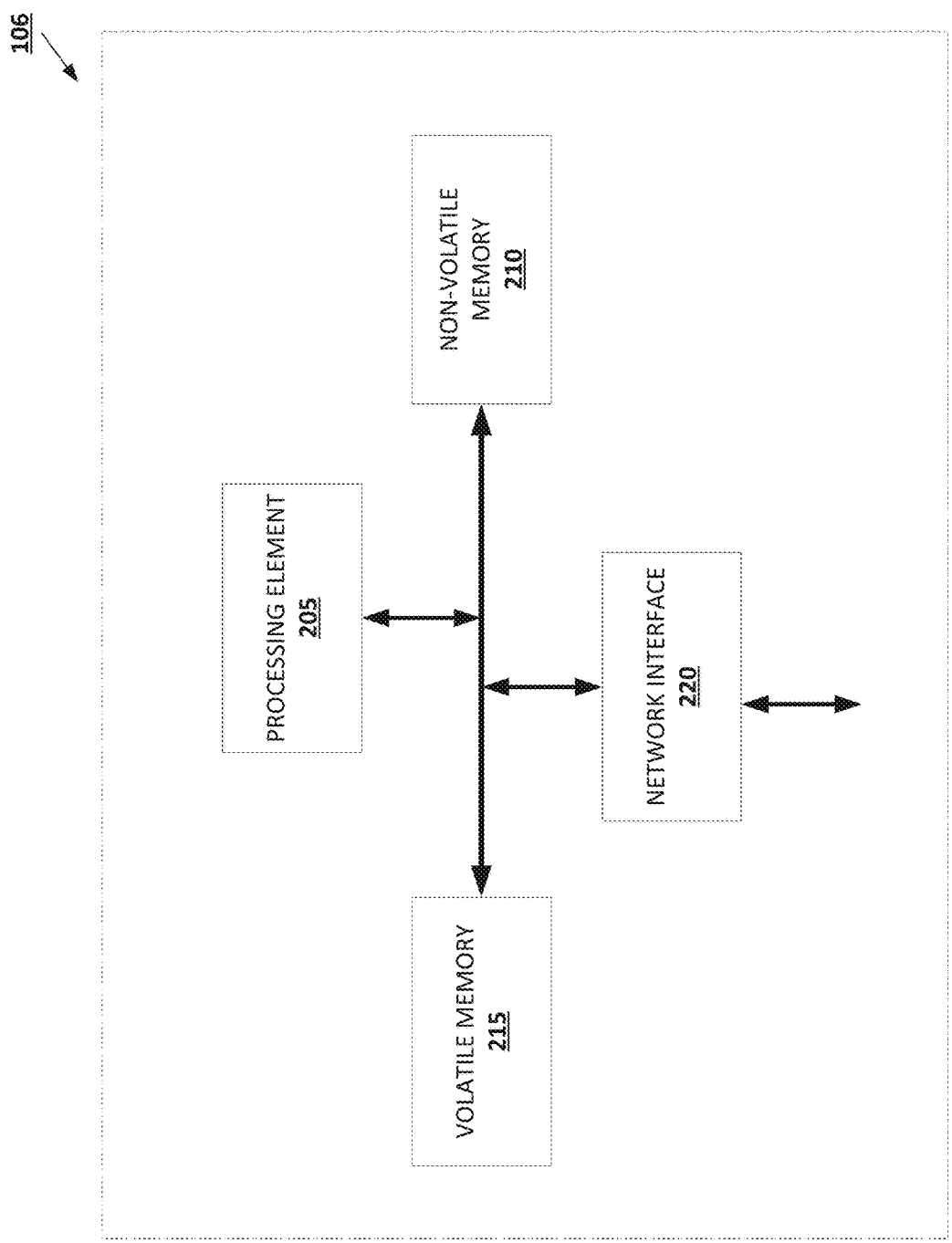

FIG. 2 provides an example NLP computing entity in accordance with some embodiments discussed herein.

Figure 3:
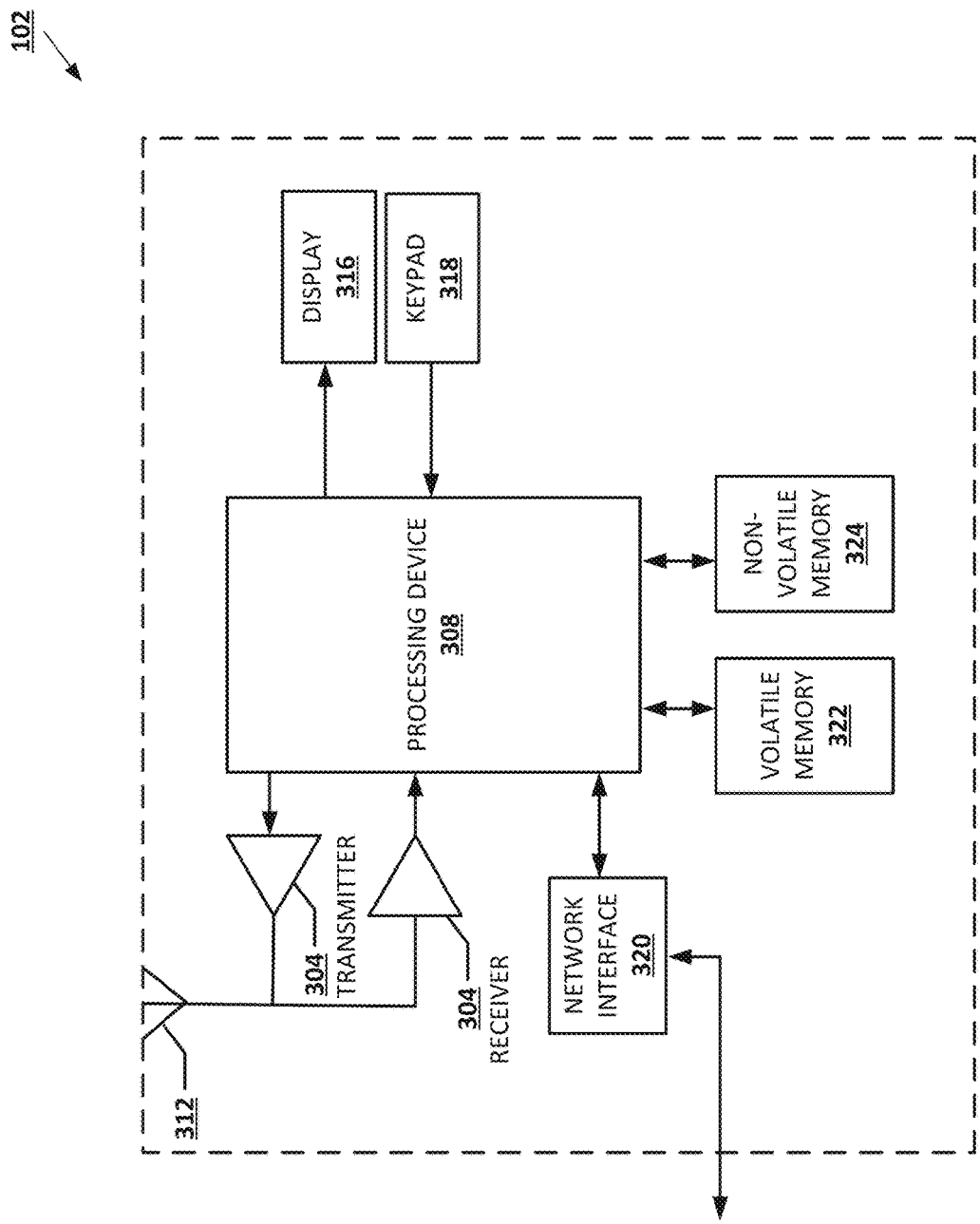

FIG. 3 provides an example external computing entity in accordance with some embodiments discussed herein.

Figure 4:
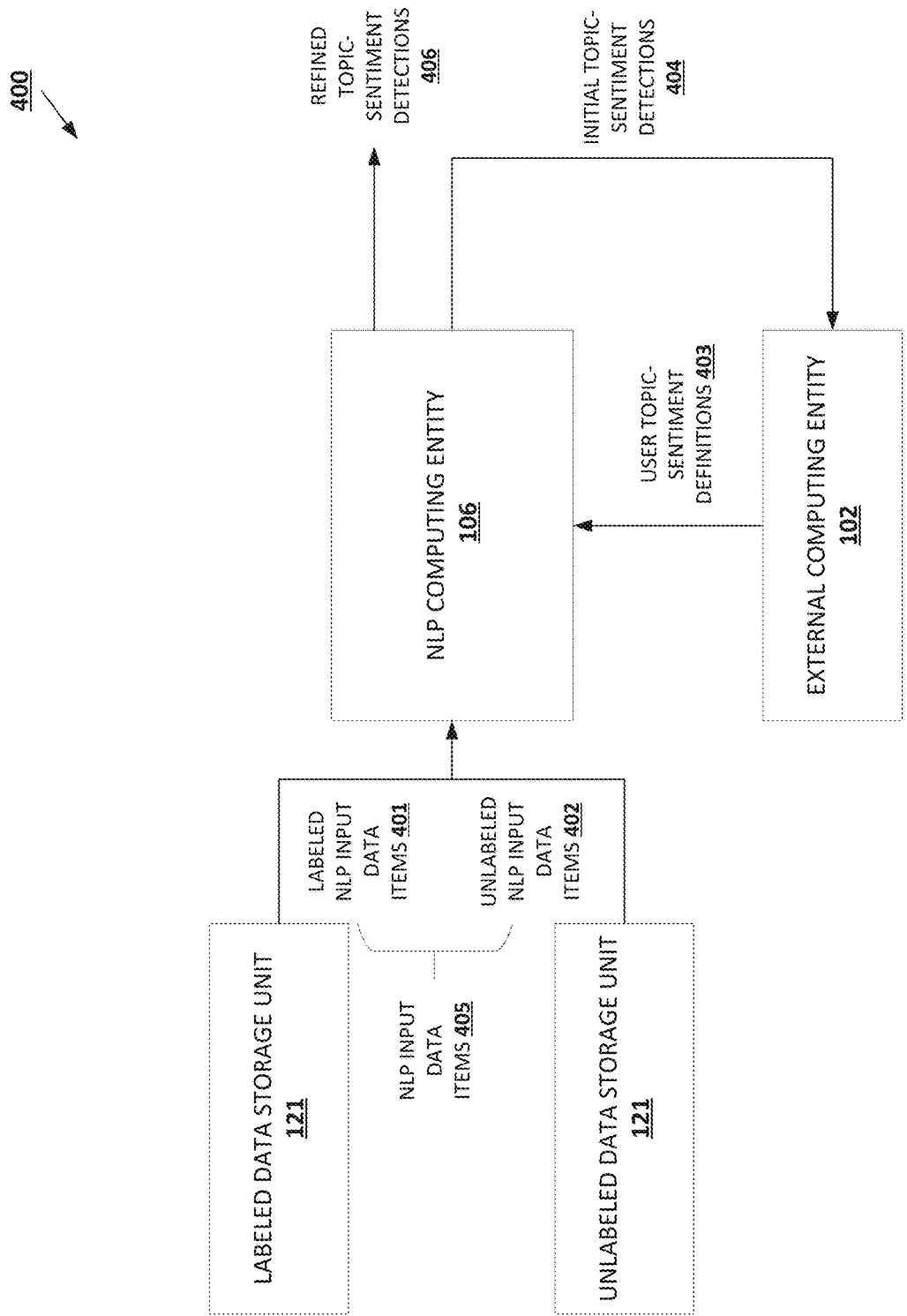

FIG. 4 is a data flow diagram of an example process for generating joint topic-sentiment detections in accordance with some embodiments discussed herein.

Figure 5:
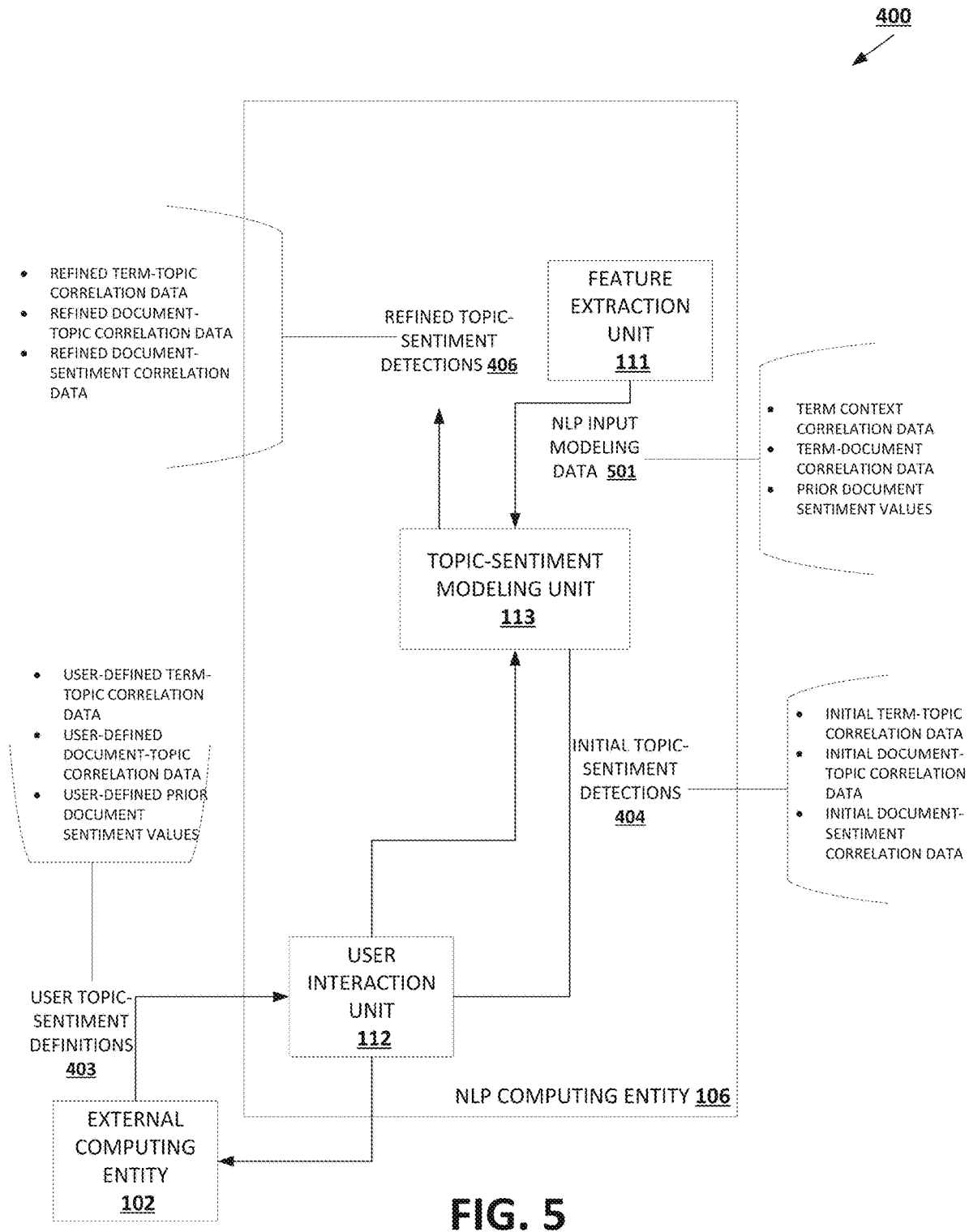

FIG. 5 is a data flow diagram of an example process for generating refined topic-sentiment detections in accordance with some embodiments discussed herein.

Figure 6:
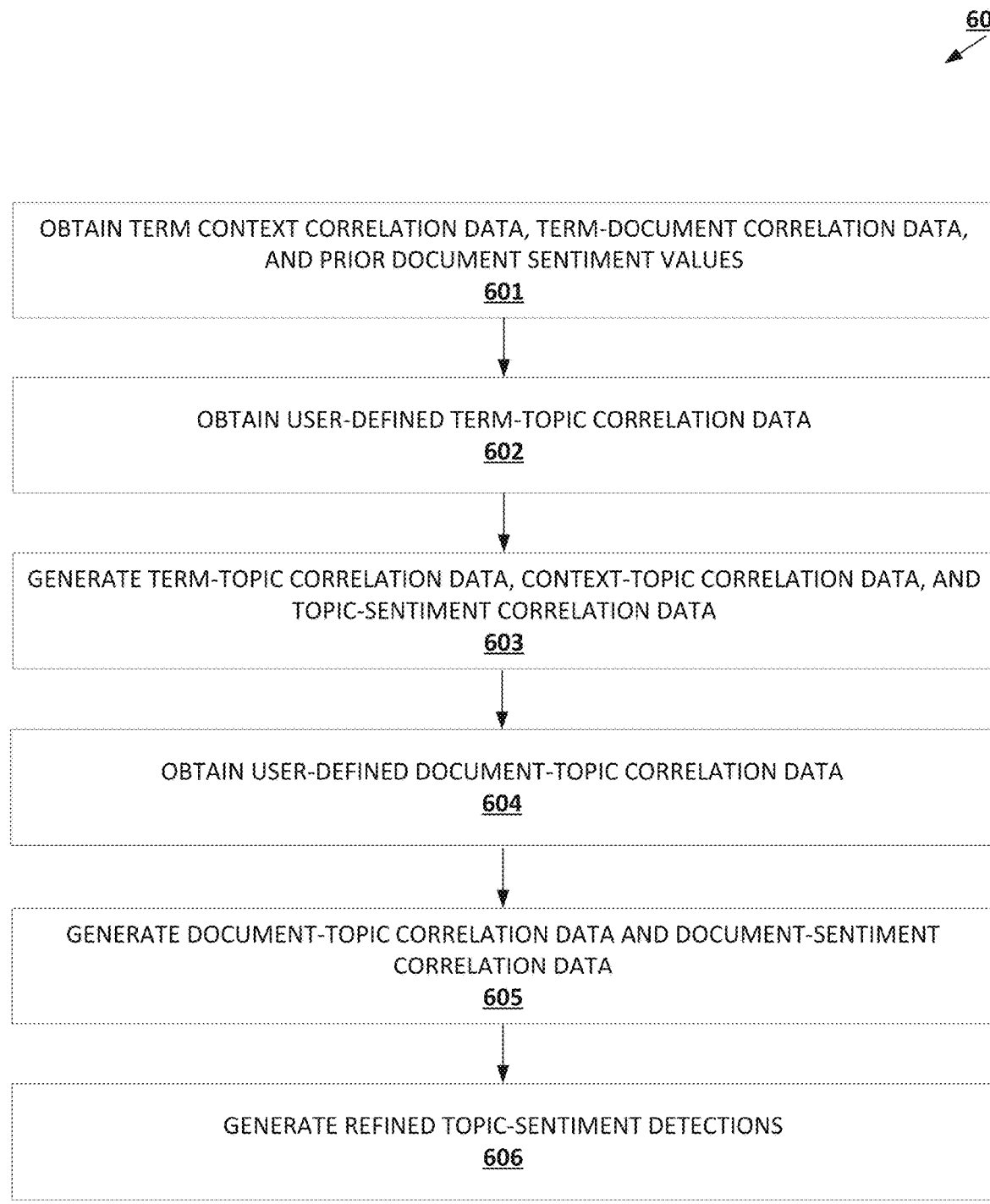

FIG. 6 is a flowchart diagram of an example process for generating joint topic-sentiment detections using factorization-based optimizations in accordance with some embodiments discussed herein.

Figure 7:
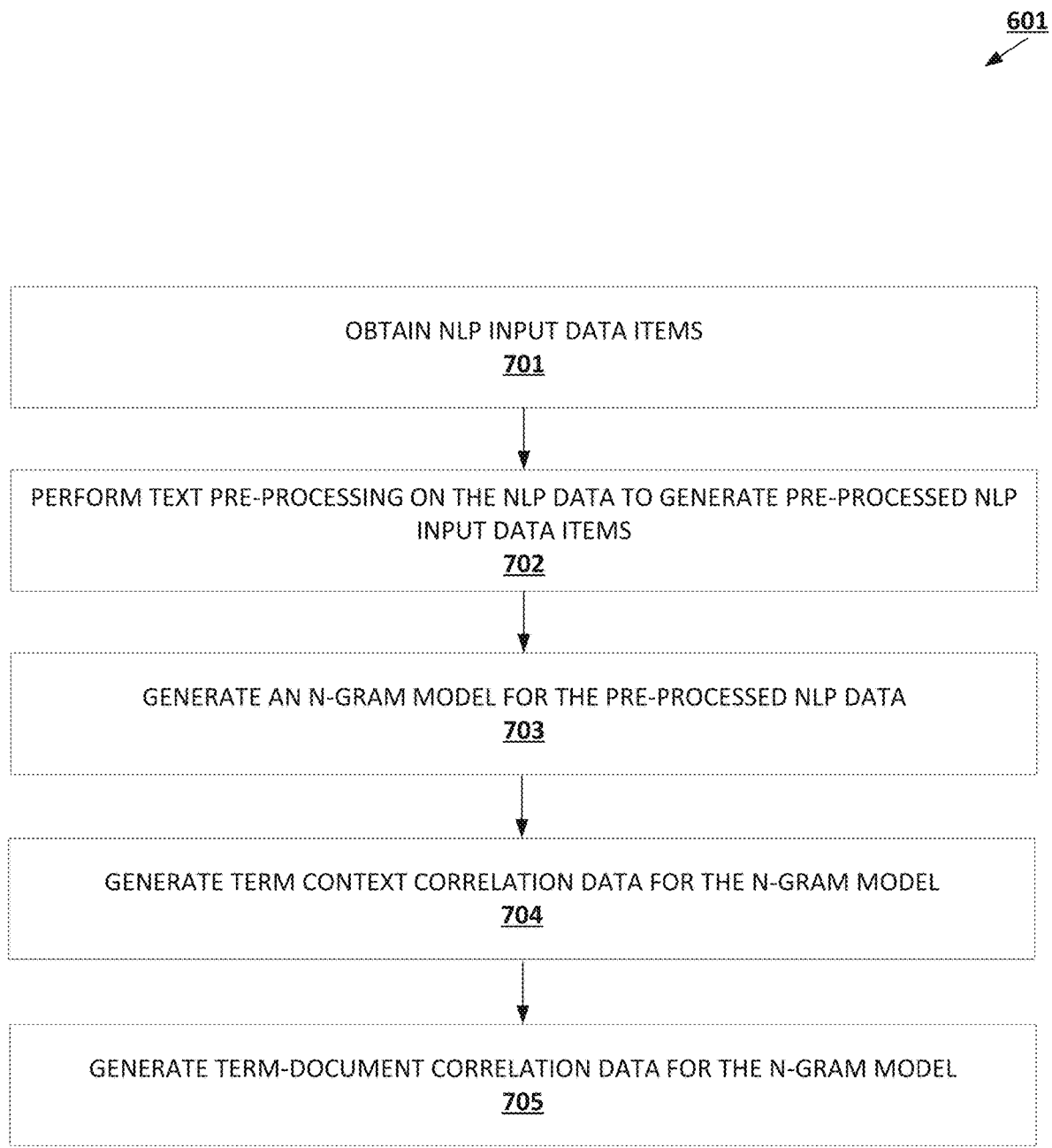

FIG. 7 is a flowchart diagram of an example process for generating term context correlation data and term-document correlation data in accordance with some embodiments discussed herein.

Figure 8:
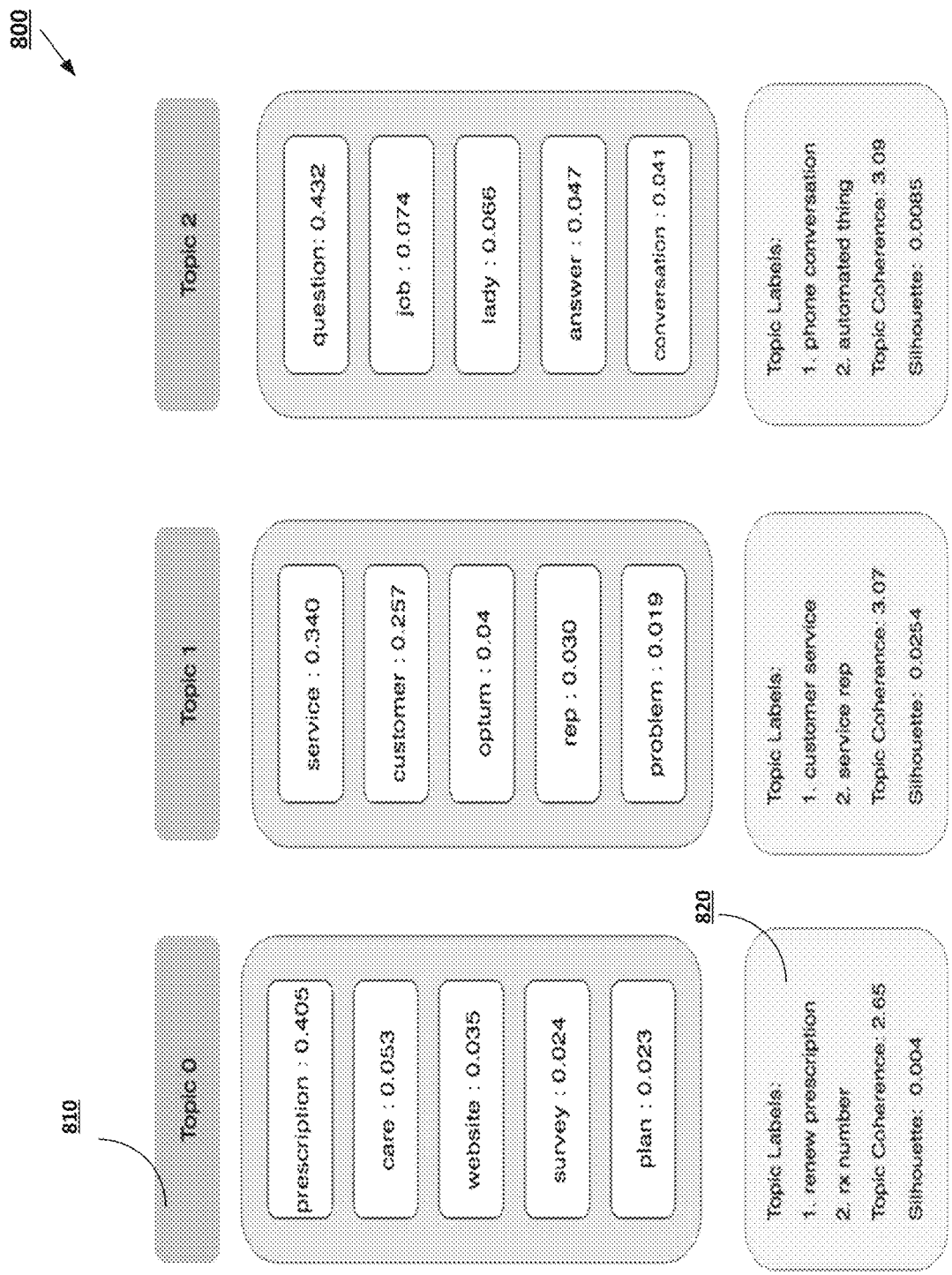

FIG. 8 provides an operational example of a topic model in accordance with some embodiments discussed herein.

Figure 9:
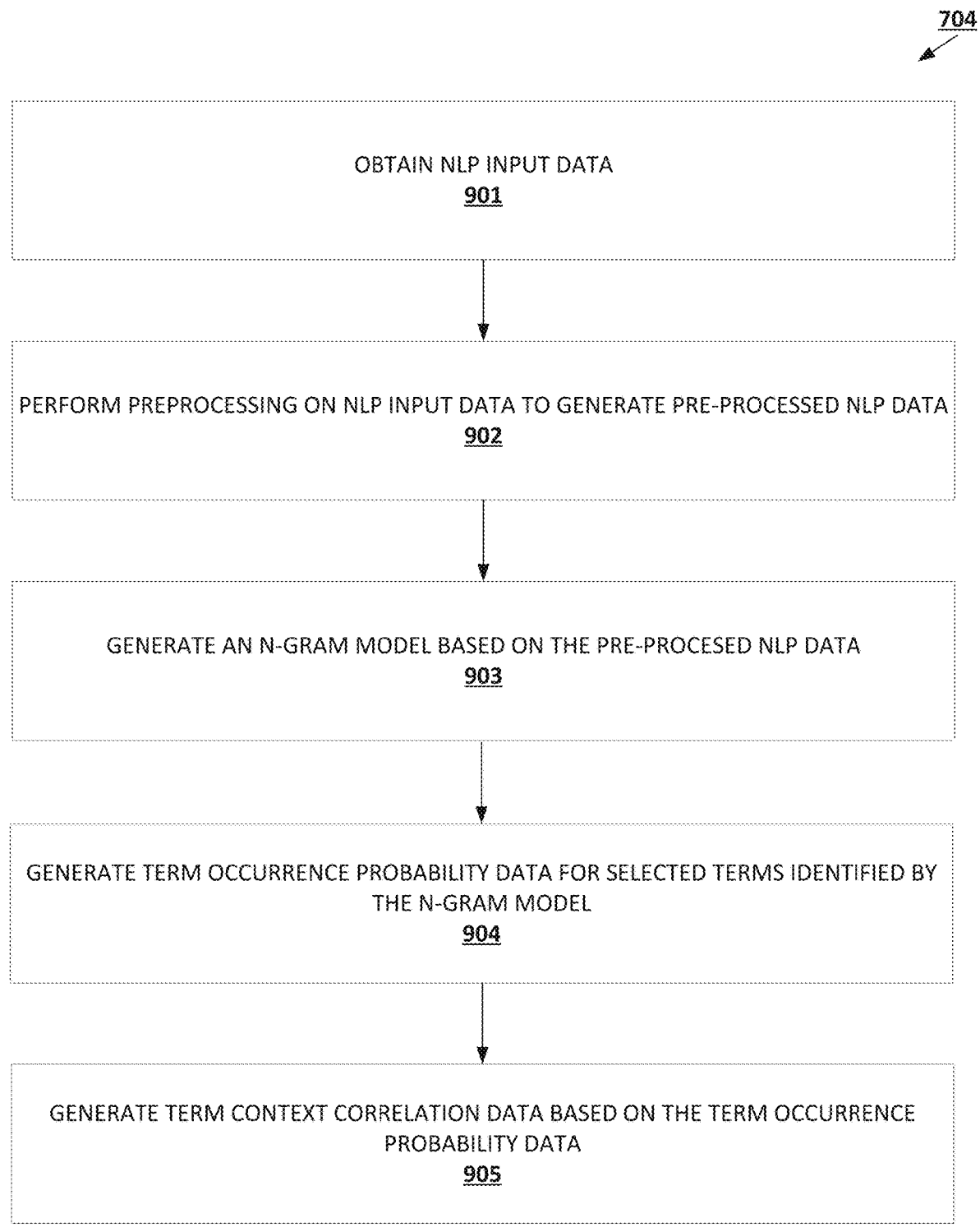

FIG. 9 is a flowchart diagram of an example process for generating term context correlation data in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media may include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also may include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also may include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also may include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an exemplary overview of an architecture 100 that can be used to practice embodiments of the present invention. The architecture 100 includes an NLP system 101 and one or more external computing entities 102, where the one or more external computing entities 102 provide NLP input data (e.g., labeled NLP input data and/or unlabeled NLP input data) to the NLP system 101, and further where the NLP system 101 generates joint topic-sentiment detections for the NLP input data and provides the joint topic-sentiment detections to the one or more external entities. In some embodiments, the NLP system 101 interacts with the one or more external computing entities 102 over a communication network (not shown). The communication network may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The NLP system 101 includes an NLP computing entity 106 and a storage subsystem 108. The NLP computing entity 106 is configured to generate joint sentiment-detections for the NLP input data stored in the storage subsystem 108. The storage subsystem 108 includes a labeled data storage unit 121 and an unlabeled data storage unit 122. The NLP computing entity 106 includes a feature extraction unit 111, a user interaction unit 112, and a topic-sentiment modeling unit 113.

The labeled data storage unit 121 is configured to store labeled NLP input data items, where labeled each NLP input data item includes an NLP input data item (e.g., a digital document with NLP data) and an associated prior sentiment label for the NLP input data item. The prior sentiment label for an NLP input data item may be an initial sentiment score for the NLP input data item determined using one or more shallow sentiment labeling techniques. The unlabeled data storage unit 122 is configured to store unlabeled NLP input data items, where each unlabeled NLP input data item includes an NLP data item that is not associated with a prior sentiment label for the NLP input data item. Each of the labeled data storage unit 121 and the unlabeled data storage unit 122 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

The feature extraction unit 111 may be configured to process the NLP input data items to generate NLP modeling data items. Examples of NLP modeling data items may include term context correlation data for the NLP modeling data items, term-document correlation data for the NLP modeling data items, and prior document sentiment values for the NLP modeling data items. In some embodiments, the prior document sentiment values may include sentiment labels stored for at least a portion of the NLP modeling data items that are stored in the labeled data storage unit 121. In some embodiments, the feature extraction unit 111 generates at least some of the sentiment labels that are stored in the labeled data storage unit 121 using one or more sentiment detection routines. In some embodiments, the feature extraction unit 111 generates at least some of the sentiment labels that are stored in the labeled data storage unit 121 based at least in part on data obtained from at least one of the external computing entities 102. In some embodiments, the prior document sentiment values are stored as part of a prior document sentiment value data object, such as a prior document sentiment value matrix and/or a prior document sentiment value vector.

The user interaction unit 112 may be configured to communicate with one or more user profiles to obtain user topic-sentiment definitions. Examples of user topic-sentiment definitions may include user-defined term-topic correlation data, user-defined document-topic correlation data, and user-defined document-sentiment correlation data. In some embodiments, the user profiles are associated with external computing entities 102, and thus communicating with the user profiles may include communicate with particular external computing entities 102. In some embodiments, the user profiles directly interact with the NLP system 101 and/or NLP computing entity 106, and thus communicating with the user profiles may include communicating with an input/output unit of the NLP computing entity 106 and/or an input/output unit of another computing entity associated with the NLP system 101.

The topic-sentiment modeling unit 113 may be configured to process the NLP modeling data to generate initial term-topic sentiment detections. Examples of initial term-topic sentiment detections may include initial term-topic correlation data, initial document-topic correlation data, and initial document-sentiment correlation data. Moreover, the topic-sentiment modeling unit 113 may be further configured to process the initial topic-sentiment detections to generate refined term-topic sentiment detections. Examples of refined term-topic sentiment detections may include refined term-topic correlation data, refined document-topic correlation data, and refined document-sentiment correlation data. To generate initial term-topic sentiment detections and/or refined term-topic sentiment detections may include performing one or more NMF-based optimizations.

In some embodiments, the NLP input data stored in the storage subsystem 108 may include feedback data, such as provider feedback data associated with a healthcare with a healthcare provider institution and/or a health insurance provider system. Moreover, in some embodiments, the NLP computing entity 106 is configured to process the feedback data to generate joint topic-sentiment detections that identify subject matters related to critical feedback and/or subject matters related to positive feedback.

A. Exemplary NLP Computing Entity

FIG. 2 provides a schematic of a NLP computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the NLP computing entity 106 may also may include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the NLP computing entity 106 may include or be in communication with one or more processing elements 205 (also referred to as processors, processing circuitry, and/or similar terms used herein interchangeably) that communicate with other elements within the NLP computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the NLP computing entity 106 may further may include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the NLP computing entity 106 may further may include or be in communication with volatile media (also referred to as volatile storage, memory, memory storage, memory circuitry and/or similar terms used herein interchangeably). In one embodiment, the volatile storage or memory may also may include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the NLP computing entity 106 with the assistance of the processing element 205 and operating system.

As indicated, in one embodiment, the NLP computing entity 106 may also may include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the NLP computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the NLP computing entity 106 may include or be in communication with one or more input elements, such as a keyboard input, a mouse input, a touch screen/display input, motion input, movement input, audio input, pointing device input, joystick input, keypad input, and/or the like. The NLP computing entity 106 may also may include or be in communication with one or more output elements (not shown), such as audio output, video output, screen/display output, motion output, movement output, and/or the like.

B. Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can may include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the NLP computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the NLP computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can may include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the NLP computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can may include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also may include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the NLP computing entity 106 and/or various other computing entities.

In another embodiment, the external computing entity 102 may include one or more components or functionality that are the same or similar to those of the NLP computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

III. OVERVIEW

Discussed herein methods, apparatus, systems, computing devices, computing entities, and/or the like for NLP analysis using sentiment detection configured to generate joint sentiment-topic detections. As will be recognized, however, the disclosed concepts can be used to perform other types of NLP analysis, including NLP analyses configured to generate non-joint NLP property predictions as well as NLP analyses configured to generate joint NLP property predictions other than joint sentiment-topic detections.

A. Technical Problems

Many existing NLP systems face substantial challenges in accurately and efficiently detecting reliable NLP inferences that map to real-world semantic conceptual frameworks, such as detecting topics that have sufficient topic coherence and/or sentiments that translate to practical applications. For example, many existing NLP systems are incapable of generating topics that have sufficient topic coherence. Topic coherence may refer to a measure of semantic significance of a topic model based at least in part on interrelatedness of term probability distributions used to define topics in that topic model. For example, a topic model that defines topics too generally may end up inferring incoherent topics and thus generate topic-based NLP detections that lack utility. Moreover, incoherently broad topics will likely have widespread associations with a wide variety of digital documents, a task that increases expected computational efficiency of document-topic mapping. Thus, because they fail to generate sufficiently coherent topics, many existing NLP systems generate outputs that are both inefficient and unreliable. As another example, many existing NLP systems are not capable of generating continuous sentiment values, a shortcoming that complicates application of those existing NLP systems to real-world environments. Without the ability to generate continuous sentiment values, many existing NLP systems require pre-analysis supply of sentiment labels which undermines usability, widespread utility, and practicality of using the noted existing NLP systems to conduct sentiment-based NLP analysis.

Furthermore, many existing NLP systems face substantial technical challenges in accurately and efficiently detecting reliable properties for relatively short NLP input data, such as detecting topics for with relatively short NLP input data and/or detecting sentiments for relatively short NLP input data. One reason behind the noted technical challenges is that, because of their limited size, relatively short NLP data produce limited valuable input feature data that can be used to accurately and efficiently detect reliable properties for relatively short NLP input data. As a result, existing NLP systems face substantial challenges with effective and efficient feature extraction from relatively short NLP input data. To combat challenges associated with limited feature extraction potentials of relatively short NLP input data, some existing NLP systems rely on computationally inefficient calculations that often require substantial storage bandwidth. Moreover, some existing NLP systems extract NLP features from relatively short NLP input data that are not sufficiently indicative of reliable properties of such data, and thus fail to provide reliable solutions for effectively and accurately reliable properties for relatively short NLP input data.

An example of relatively short NLP input data is feedback data associated with many healthcare systems. Many cooperative healthcare systems aim to transform health care delivery into a mission-driven, patient-centered, value-enhancing system of care. Feedback data, such as patient feedback data and/or provider feedback data could serve as a valuable yardstick for this transformation process. By mining such feedback data, an NLP system can extract customers' sentiment and opinion towards the quality of service they have received from the healthcare providers. However, because of the limitations of many existing NLP systems in accurately and efficiently detecting reliable properties for relatively short NLP input data, they are ill-suited for feedback processing in healthcare systems. As the discussed examples demonstrate, many existing NLP systems face technical challenges in accurately and efficiently detecting reliable properties for relatively short feedback data associated with healthcare systems.

Moreover, many existing NLP systems face significant technical drawbacks in accurately analyzing sentiment information about feedback data to detect relevant semantic properties for such feedback data. For example, many existing NLP systems use supervised learning based at least in part on preexisting sentiment-labeled NLP documents to generate sentiment labels for new NLP documents. However, the generated sentiment labels are often poor descriptors of overall semantic structure of the NLP documents. In some cases, while existing NLP systems can provide some useful sentiment information about feedback data, they fail to properly categorize such sentiments in the context of subject-matter-specific features of such feedback data. Thus, many existing NLP systems face technical challenges related to accurately utilizing sentiment information about feedback data in order to detect relevant semantic properties for such feedback data.

B. Technical Solutions

Various embodiments of the present invention address technical challenges related to accurately and efficiently detect reliable NLP inferences that map to real-world semantic conceptual frameworks by enabling user-defined modeling data to affect the overall NLP analysis. For example, various embodiments of the present invention enable user-defined topic models and/or sentiment values to be provided to an NLP module to enable NLP analysis based at least in part on an intelligent and refined semantic model. Through describing innovative techniques for using such user-defined NLP modeling data as an input to an NLP refinement process, various embodiments of the present invention generate topics that have greater topic coherence as well as reliable sentiment values. Importantly, various embodiments of the present invention accomplish this goal while avoiding efficiency challenges of the many existing NLP systems, such as existing NLP systems that perform excessive textual processing because of deficiencies in their topic modeling and/or sentiment modeling. In addition, various embodiments of the present invention further increase efficiency and/or reliability of NLP systems by enabling continuous sentiment detection, which better maps to many real-world applications and processing systems.

In addition, various embodiments of the present invention address technical challenges related to accurately and efficiently detecting reliable properties for relatively short NLP input data, including feedback data associated many healthcare systems, by utilizing NLP models that detect important features from NLP data using groups of interconnected factorization-based optimizations. For example, various embodiments of the present invention use optimization of non-negative matrix factorization (NMF) models. By utilizing NMF models, various embodiments of the present invention effectively and efficiently relate raw feature data associated with NLP data to more sophisticated correlation models that describe semantically deeper inferences about the NLP data. In doing so, various embodiments of the present invention address technical drawbacks of many existing NLP systems in accurately and efficiently detecting reliable properties for relatively short NLP input data, including feedback data associated many healthcare systems.

In some embodiments, disclosed NLP systems address relative shortness of NLP input data by factoring feature data (e.g., term correlation data for the unlabeled feedback data) for the NLP input data using NMF-based optimization to generate term-topic correlation data, rather by utilizing high-dimensional and sparse term occurrence information associated with the NLP input data to generate term-topic correlation data. This alone provides substantial efficiency advantages (e.g., by reducing the need for utilizing storage-intensive and computationally-complex data such as the high-dimensional and sparse term occurrence information associated with NLP input data) as well as substantial accuracy advantages (e.g., by providing extraction of more reliable and more semantically representative features associated with NLP input data) compared to many existing NLP systems. Moreover, in some embodiments, subsequent to the above-noted NMF-based optimization to generate term-topic correlation data, the disclosed NLP systems detect document-topic correlation data from the term-document correlation data using another NMF-based optimization, thus further expanding the efficiency and accuracy advantages offered by various embodiments of the present invention in accurately and efficiently detecting reliable properties for relatively short NLP input data, including feedback data associated many healthcare systems.

Moreover, various embodiments of the present invention address technical challenges related to accurately analyzing sentiment information about feedback data to detect relevant semantic properties for such feedback data by jointly detecting topic and sentiment designations for such feedback data. In some embodiments, disclosed NLP systems perform topic detection using constrained-NMF-based models and perform sentiment detection using constrained-3-factor-NMF-based models. In doing so, the disclosed NLP systems provide solutions for accurately detecting relevant semantic properties for feedback data, such as healthcare-related feedback data, where the provided solutions can be integrated in existing feedback processing systems without the need to modify underlying feedback gathering and processing mechanisms. Accordingly, by disclosing solutions for jointly detecting topic and sentiment designations for feedback data, various embodiments of the present invention address technical challenges related to accurately analyzing sentiment information about feedback data to detect relevant semantic properties for such feedback data.

IV. EXEMPLARY SYSTEM OPERATION

Various embodiments of the present invention address technical challenges related to accurately and efficiently detect reliable NLP inferences that map to real-world semantic conceptual frameworks by enabling user-defined modeling data to affect the overall NLP analysis. For example, various embodiments of the present invention enable user-defined topic models and/or sentiment values to be provided to an NLP module to enable NLP analysis based at least in part on an intelligent and refined semantic model. Through describing innovative techniques for using such user-defined NLP modeling data as an input to an NLP refinement process, various embodiments of the present invention generate topics that have greater topic coherence as well as reliable sentiment values. Importantly, various embodiments of the present invention accomplish this goal while avoiding efficiency challenges of the many existing NLP systems, such as existing NLP systems that perform excessive textual processing because of deficiencies in their topic modeling and/or sentiment modeling. In addition, various embodiments of the present invention further increase efficiency and/or reliability of NLP systems by enabling continuous sentiment detection, which better maps to many real-world applications and processing systems.

FIG. 4 is a data flow diagram of an example process 400 for generating joint topic-sentiment detections for each of one or more unlabeled NLP input data items 402. Via the various steps/operations of process 400, a system of one or more computers (e.g., the NLP system 101 of FIG. 1) can perform joint topic-sentiment detection for NLP inputs based at least in part on user topic-sentiment definitions.

The process 400 begins when the NLP computing entity 106 receives the one or more unlabeled NLP input data items 402 from the unlabeled data storage unit 122 and one or more labeled NLP input data items 401 from the labeled data storage unit 121. In some embodiments, a labeled NLP input data item 401 is a collection of data (e.g., a collection of text data, such as a digital document) that is associated with a pre-existing sentiment value (where the pre-existing sentiment value for the labeled NLP input data item 401 may be part of the labeled NLP input data item 401), while an unlabeled NLP input data item 401 is a collection of data that is not associated with a preexisting sentiment value. In some embodiments, the NLP computing entity 106 is configured to use the labeled NLP input data items 401 and the unlabeled NLP input data items 402 (collectively, the NLP input data items 405) to determine at least one of one or more initial topic-sentiment detections 404 and one or more refined topic-sentiment detections 406 for each of the unlabeled NLP input data items 402. In some embodiments, the storage system 108 is configured to retrieve at least some of the unlabeled NLP input data items 402 and/or at least some of labeled NLP input data items 401 from one or more external computing entities 102.

The process 400 continues when the NLP computing entity 106 uses the NLP input data items 405 to determine initial topic-sentiment detections 404 for the unlabeled NLP input data items 402. In some embodiments, an initial topic-sentiment detection 404 for an unlabeled NLP input data item 402 is any collection of data items (e.g., a collection that includes one or more initial topic-sentiment data objects such as one or more initial topic-sentiment matrices) that describes at least one aspect of a topic detection associated with the unlabeled NLP input data item 402 and/or at least one aspect of a sentiment detection associated with the unlabeled NLP input data item 402, where the at least one aspect of the topic detection and/or the at least one aspect of the sentiment detection is determined without regard to user topic-sentiment definitions 403 for the NLP input data item 405.

In some embodiments, an initial topic-sentiment detection 404 for a particular NLP input data item 405 is determined based at least in part on at least one of automatically-generated feature data for the NLP input data items 405 and/or pre-configured ground-truth data for the NLP input data items 405. For example, an initial topic-sentiment detection 404 for an NLP input data item 405 may be determined based at least in part on at least one of automatically-generated term context correlation data for the NLP input data items 405, automatically-generated term-document correlation data for the NLP input data items 405, and a pre-configured prior document sentiment value for the NLP input data item 405. In some embodiments, the initial topic-sentiment detections 404 for the NLP input data items 405 may include at least one of initial term-topic correlation data for the NLP input data items 405 determined without regard to the user topic-sentiment definitions 403 for the NLP input data items 405, initial document-topic correlation data for the NLP input data items 405 determined without regard to the user topic-sentiment definitions 403 for the NLP input data items 405, and initial document-sentiment correlation data for the NLP input data items 405 determined without regard to the user topic-sentiment definitions 403 for the NLP input data items 405.

In some embodiments, to determine the initial topic-sentiment detections 404 for the unlabeled NLP input data items 402, the NLP computing entity 106 performs some of the steps/operations depicted in process 500 of FIG. 5. As depicted in process 500, to determine the initial topic-sentiment detections 404 for the unlabeled NLP input data items 402, the feature extraction unit generates NLP input modeling data 501 (e.g., based at least in part on the NLP input data items 405) and the topic-sentiment modeling unit 113 of the NLP computing entity 106 receives the NLP input modeling data 501 from the feature extraction unit 111. The NLP input modeling data 501 may include term-context correlation data, term-document correlation data, and/or prior document sentiment values.

In some embodiments, the term-context correlation data may include one or more term-context correlation data objects (e.g., a term-context correlation matrix) that indicate, for each term of selected terms associated with the NLP input data items 405, a context indicator associated with occurrence of the term in the NLP input data items 405, where a context indicator for a particular selected term may indicate a corresponding likelihood of co-occurrence of the particular selected term with groups of one or more other selected terms. In some embodiments, the term-document correlation data may include one or more term-document correlation data objects (e.g., a term-document correlation matrix) that indicate, for each term of one or more selected terms associated with the NLP input data items 405 and each digital document of one or more digital documents associated with the NLP input data items 405, a corresponding term-document correlation indicator, where a term-document correlation indicator for a particular selected term and a particular digital document is a measure of presence or absence of the particular selected term in the digital document and/or a measure of extent of occurrence of the particular selected term in the digital document.

In some embodiments, the prior document sentiment values may include one or more prior sentiment value data objects (e.g., a prior sentiment value matrix) that indicate, for each of one or more digital documents associated with the NLP input data items 405, a preexisting sentiment value, such as a preexisting discrete sentiment value and/or a preconfigured concrete sentiment value. In some embodiments, the prior document sentiment values are determined based at least in part on the pre-existing sentiment values associated with the labeled NLP input data items 401. In some embodiments, the one or more prior sentiment value data objects (e.g., a prior sentiment value matrix) indicate the following: (i) for each of one or more labeled NLP input data items 401, a prior sentiment label, and (ii) for each of the one or more unlabeled NLP input data items 402, designated prior sentiment labels (e.g., null prior sentiment labels).

As further depicted in process 500 of FIG. 5, the topic-sentiment modeling unit 113 utilizes the NLP input modeling data 501 to generate the initial topic-sentiment detections 404 and provide the initial topic-sentiment detections 404 to the external computing entity 102. In some embodiments, the initial topic-sentiment detections 404 generated by the topic-sentiment modeling unit 113 may include initial term-topic correlation data, initial document-topic correlation data, and/or initial document-sentiment correlation data.

In some embodiments, the initial term-topic correlation data may include one or more initial term-topic correlation data objects (e.g., an initial term-topic correlation matrix) that indicate, for each term of selected terms associated with the NLP input data items 405 and each topic of a group of topics, one or more initial term-topic correlation indicators. In some embodiments, the initial term-topic correlation indicator for a particular selected term and a particular topic indicates an estimated relatedness of the particular term and the particular topic, where the estimated relatedness is determined without regard to user topic-sentiment definitions 403 for particular NLP input data items 405 (e.g., is determined solely based at least in part on the NLP input modeling data 501 for the particular NLP input data items 405).

In some embodiments, the initial document-topic correlation data may include one or more initial document-topic correlation data objects (e.g., an initial document-topic correlation matrix) that indicate, for each digital document of a group of digital documents associated with the NLP input data items 405 and each topic of a group of topics, one or more initial document-topic indicators. In some embodiments, the initial term-topic correlation indicator for a particular digital document and a particular topic indicates an estimated relatedness of the particular digital document and the particular topic, where the estimated relatedness is determined without regard to user topic-sentiment definitions 403 for particular NLP input data items 405 (e.g., is determined solely based at least in part on the NLP input modeling data 501 for the particular NLP input data items 405).

In some embodiments, the initial document-sentiment correlation data may include one or more initial document-sentiment correlation data objects (e.g., an initial document-sentiment correlation matrix) that indicate, for each digital document of a group of digital documents associated with the NLP input data items 405, a corresponding initial sentiment value (e.g., a discretely-defined initial sentiment value and/or a continuously-defined initial sentiment value). In some embodiments, the initial sentiment value for each digital document is determined without regard to user topic-sentiment definitions 403 for particular NLP input data items 405 (e.g., is determined solely based at least in part on the NLP input modeling data 501 for the particular NLP input data items 405).

Returning to FIG. 4, after generating the initial topic-sentiment detections 404, the NLP computing entity 106 provides the initial topic-sentiment detections 404 to a particular external computing entity 102 associated with an administrator user profile. The external computing entity 102 then generates user topic-sentiment definitions 403 based at least in part on user actions by the administrator user profile and provides the generated user topic-sentiment definitions 403 to the NLP computing entity 106. In some embodiments, the user topic-sentiment definitions 403 indicate at least one user request to change at least a part of the initial topic-sentiment detections. For example, the user topic-sentiment definitions 403 may indicate a user request to change at least a portion of at least one of initial term-topic correlation data, initial document-topic correlation data, and initial document-sentiment correlation data.

In some embodiments, to obtain user topic-sentiment definitions 403, the NLP computing entity 106 performs some of the steps/operations depicted in process 500 of FIG. 5. As depicted in process 500, the user interaction unit 112 of the NLP computing entity 106 receives user topic-sentiment definitions 403 from an external computing entity 102. Despite the fact that the exemplary embodiments presented in FIGS. 5-6 depict the user topic-sentiment definitions 403 from an external computing entity, one of ordinary skill in the art will recognize that the user topic-sentiment definitions 403 may be generated based at least in part on direct user interactions between an administrator user profile and the NLP system 101 and/or direct user interactions between an administrator user profile and the NLP computing entity 106. Indeed, one of ordinary skill in the art will recognize that the user topic-sentiment definitions 403 may include modifications to at least a part of the initial topic-sentiment detections 404 that are not generated based at least in part on any user interactions, such as automatically-generated medications (e.g., automatically-generated modifications that are generated using a machine learning routine).

As further depicted in process 500 of FIG. 5, the user topic-sentiment definitions 403 may include one or more of user-defined term-topic correlation data, user-defined document-topic correlation data, and user-defined document sentiment values. In some embodiments, the user-defined term-topic correlation data may include one or more user-defined term-topic correlation data objects (e.g., a user-defined term-topic correlation matrix) that indicated at least one requested modification to the initial term-topic correlation data discussed above with reference to the initial topic-sentiment detections 404. In some embodiments, the user-defined term-document correlation data may include one or more user-defined term-document correlation data objects (e.g., a user-document term-topic correlation matrix) that indicated at least one requested modification to the initial term-document correlation data discussed above with reference to the initial topic-sentiment detections 404. In some embodiments, the user-defined sentiment values may include one or more user-defined sentiment value data objects (e.g., a user-defined sentiment value matrix) that indicate at least one requested modification to at least one prior document sentiment value discussed above with reference to the initial topic-sentiment detections 404.

In some embodiments, to modify the initial term-topic correlation data, the user topic-sentiment definitions 403 can modify at least one initial term-topic correlation indicator associated with a topic and a term. As depicted in the exemplary topic model 800 of FIG. 8, a topic may be defined by one initial term-topic correlation indicator, where an initial term-topic correlation indicator may define a predicted relatedness degree between a corresponding term and a corresponding topic. For example, as depicted in the topic model 800, topic 0 810 is associated with five initial term-topic correlation indicators 0.405, 0.503, 0.035, 0.024, and 0.023 for the terms "prescription," "care," "website," "survey," and "plan" respectively. The noted distribution of the initial term-topic correlation indicators may indicate that (for example) the presence of the term "prescription" in an NLP data item 405 is deemed more predictive of a relatedness between the NLP input data item 405 to topic 0 810 than the presence of the term "website" in the NLP data item 405, since the initial term-topic correlation indicator for topic 0 810 and the term "prescription" (e.g., 0.405) is higher than the initial term-topic correlation indicator for topic 0 810 and the term "website" (e.g., 0.035). Moreover, topic 0 is associated with topic labels 820 "renew prescription" and "rx number."

In some embodiments, the user topic-sentiment definitions 403 can modify the initial term-topic correlation data by performing one or more of the following: (i) changing particular initial term-topic correlation indicators for a particular topic, (ii) merging two or more topics into one topic by combining their initial term-topic correlation indicators (e.g., averaging their pre-merge initial term-topic correlation indicators to generate merged initial term-topic correlation indicators), and (iii) splitting a topic into two or more topics by dividing their pre-split initial term-topic correlation indicators between the resulting two or more topics. Through one or more of the noted operations, an administrator user profile can request modification of the initial term-topic correlation matrix.

Returning to FIG. 4, the NLP computing entity 106 can generate refined topic-sentiment detections 406 for the unlabeled NLP input data items 402 based at least in part on the initial topic-sentiment detections 404 for the NLP input data items 405 and the user topic-sentiment definitions 403 for the NLP input data items 405. In some embodiments, a refined topic-sentiment detection 406 for a unlabeled input data item 402 is any collection of data items (e.g., a collection that includes one or more refined topic-sentiment data objects such as one or more refined topic-sentiment matrices) that describes at least one aspect of a topic detection associated with the unlabeled NLP input data item 402 and/or at least one aspect of a sentiment detection associated with the unlabeled NLP input data item 402, where the at least one aspect of the topic detection and/or the at least one aspect of the sentiment detection is determined based at least in part on one or more modifications to the initial topic-sentiment detections 404 for the NLP input data items 405, and where the one or more modifications are in turn determined based at least in part on user topic-sentiment definitions 403 for the NLP input data item 405. In some embodiments, the refined topic-sentiment detections 406 for the NLP input data items 405 may include at least one of refined term-topic correlation data for the NLP input data items 405 determined based at least in part on the user topic-sentiment definitions 403 for the NLP input data items 405, refined document-topic correlation data for the NLP input data items 405 determined based at least in part on the user topic-sentiment definitions 403 for the NLP input data items 405, and refined document-sentiment correlation data for the NLP input data items 405 determined based at least in part on the user topic-sentiment definitions 403 for the NLP input data items 405.

In some embodiments, the NLP computing entity 106 may generate refined topic-sentiment detections 406 by performing some of the steps/operations depicted in the process 500 of FIG. 5. As depicted in FIG. 5, the topic-sentiment modeling unit 113 of the NLP computing entity 106 utilizes the initial topic-sentiment detections 404 and the user topic-sentiment definitions 403 to generate refined topic-sentiment detections 406. As further depicted in FIG. 5, the refined topic-sentiment detections 406 may include at least one of refined term-topic correlation data, refined document-topic correlation data, and refined document-sentiment correlation data.

In some embodiments, the refined term-topic correlation data may include one or more refined term-topic correlation data objects (e.g., a refined term-topic correlation matrix) that indicate, for each term of selected terms associated with the NLP input data items 405 and each topic of a group of topics, one or more refined term-topic correlation indicators. In some embodiments, the refined term-topic correlation indicator for a particular selected term and a particular topic indicates an estimated relatedness of the particular term and the particular topic, where the estimated relatedness is determined based at least in part on user topic-sentiment definitions 403 for particular NLP input data items 405.

In some embodiments, the refined document-topic correlation data may include one or more refined document-topic correlation data objects (e.g., a refined document-topic correlation matrix) that indicate, for each digital document of a group of digital documents associated with the NLP input data items 405 and each topic of a group of topics, one or more initial document-topic indicators. In some embodiments, the refined term-topic correlation indicator for a particular digital document and a particular topic indicates an estimated relatedness of the particular digital document and the particular topic, where the estimated relatedness is determined based at least in part on user topic-sentiment definitions 403 for particular NLP input data items 405.

In some embodiments, the refined document-sentiment correlation data may include one or more refined document-sentiment correlation data objects (e.g., a refined document-sentiment correlation matrix) that indicate, for each digital document of a group of digital documents associated with the NLP input data items 405, a corresponding refined sentiment value (e.g., a discretely-defined refined sentiment value and/or a continuously-defined refined sentiment value). In some embodiments, the sentiment value for each digital document is determined based at least in part on user topic-sentiment definitions 403 for the particular NLP input data items 405.

In some embodiments, to generate refined topic-sentiment detections 406 for the unlabeled NLP input data items 402 based at least in part on the initial topic-sentiment detections 404 for the NLP input data items 405 and the user topic-sentiment definitions 403 for the NLP input data items 405, the NLP computing entity 106 performs the steps/operations of process 600 depicted in FIG. 6. The process 600 begins at step/operation 601 when the NLP computing entity 106 (e.g., the feature extraction unit 111 of the NLP computing entity 106) obtains term-context correlation data (e.g., a term-context correlation matrix), term-document correlation data (e.g., a term-document correlation matrix), and prior document sentiment values (e.g., a prior document sentiment vector and/or a prior document sentiment matrix).

In some embodiments, a prior document sentiment vector is a vector that includes, for each digital document associated with the NLP input data items 405, a prior sentiment value, such as a discretely-defined prior sentiment value and/or a continuously-defined prior sentiment value. In some embodiments, a prior document sentiment matrix is a matrix that includes, for each digital document associated with the NLP input data items 405 and each sentiment label of a group of sentiment labels, an association score between the digital document and the sentiment document, such as a discretely-defined association score and/or a continuously-defined association score. In some embodiments, the NLP computing entity 106 generates the prior document sentiment values by utilizing the feature extraction unit 111, which in turn may obtain the prior document sentiment values from one or more external computing entities 102 and/or may generate the prior document sentiment values based at least in part on one or more preliminary sentiment evaluation routines, such as a naïve sentiment evaluation routine and/or a sentiment evaluation routine that utilizes net promoter scores (NPSs) for digital documents associated with the NLP input data items 405.

In some embodiments, the NLP computing entity 106 generates the term context correlation data and the term-document correlation data using the feature extraction unit 111, which may in turn analyze the NLP input data items 405 to determine a term co-occurrence distribution of co-occurrences of selected terms in the NLP input data items 405, determine a term-document distribution of occurrences of selected terms in digital documents associated with the NLP input data items 405, determine the initial term-context correlation matrix based at least in part on the term co-occurrence distribution, and determine the initial term-document correlation data based at least in part on the term-document distribution.

In some embodiments, the NLP computing entity 106 (e.g., the feature extraction unit 111 of the NLP computing entity 106) performs process in accordance with the various steps/operations depicted in FIG. 7. The process depicted in FIG. 7 begins at step/operation 701 when the NLP computing entity 106 obtains the NLP input data items 405. At step/operation 702, the NLP computing entity 106 performs text pre-processing on the NLP input data items 405 to generate pre-processed NLP input data items. Examples of pre-processing tasks performed on the NLP input data items 405 to generate the pre-processed NLP input data items may include shallow NLP tasks such as chunking, shallow parsing, and/or tokenizing.

At step/operation 703, the NLP computing entity 106 generates an n-gram model for the pre-processed NLP input data items, where the n-gram model may identify one or more n-grams (e.g., unigrams, bi-grams, where n may be determined by system configuration data) in the pre-processed NLP input data items. An n-gram may be a combination of one or more words and/or semantic tokens. In this disclosure, the terms "n-gram" and "term" have been used interchangeably. In some embodiments, to generate the n-gram model for the pre-processed NLP input data items, the NLP computing entity 106 may utilize one or more syntactic indicators of n-grams (e.g., whitespace characters). In some embodiments, to generate the n-gram model for the pre-processed NLP input data items, the NLP computing entity 106 may utilize a sematic model of the pre-processed NLP input data items, such as a semantic model determined using part-of-speech tagging.

At step/operation 704, the NLP computing entity 106 generates term context correlation data for one or more selected terms, where the one or more selected terms may include at least some of the terms identified by the n-gram model. In some embodiments, the term context correlation data may include a term context correlation matrix that indicates, for each pair of selected terms, a similarity measure for the pair based at least in part on a co-occurrence probability of the pair in the NLP input data items 405.

In some embodiments, the NLP computing entity 106 generates the term context correlation data in accordance with process depicted in FIG. 9. The process depicted in FIG. 9 begins at step/operation 901 when the NLP computing entity 106 obtains the NLP input data items 405. At step/operation 902, the NLP computing entity 106 performs pre-processing on the NLP input data items 405 to generate pre-processed NLP input data items. Examples of pre-processing tasks performed on the NLP input data items 405 to generate the pre-processed NLP input data items may include shallow NLP tasks such as chunking, shallow parsing, tokenizing, and/or the like.

At step/operation 903, the NLP computing entity 106 generates an n-gram model for the pre-processed NLP input data items, where the n-gram model may identify one or more n-grams (e.g., unigrams, bigrams, where n may be determined by system configuration data) in the pre-processed NLP input data items. An n-gram may be a combination of one or more words and/or semantic tokens. In this disclosure, the terms "n-gram" and "term" have been used interchangeably. In some embodiments, to generate the n-gram model for the pre-processed NLP input data items, the NLP computing entity 106 may utilize one or more syntactic indicators of n-grams (e.g., whitespace characters). In some embodiments, to generate the n-gram model for the pre-processed NLP input data items, the NLP computing entity 106 may utilize a sematic model of the pre-processed NLP input data items, such as a semantic model determined using part-of-speech tagging.

At step/operation 904, the NLP computing entity 106 generates term occurrence probability data for one or more selected terms, where the one or more selected terms may include at least some of the terms identified by the n-gram model. In some embodiments, the term occurrence probability data for the selected terms include: (i) a singular occurrence probability for each selected term and (ii) a corresponding joint occurrence probability for each pair of selected terms. For example, given three selected terms $t_i$, $t_j$, and $t_k$, the NLP computing entity 106 may generate a singular occurrence probability $P(t_i)$ for the term $t_i$, a singular occurrence probability $P(t_j)$ for the term $t_j$, a singular occurrence probability $P(t_k)$ for the term $t_k$, a joint occurrence probability $P(t_i, t_j)$ for the terms $t_i$ and $t_j$, a joint occurrence probability $P(t_i, t_k)$ for the terms $t_i$ and $t_k$, and a joint occurrence probability $P(t_j, t_k)$ for the terms $t_j$ and $t_k$.

In some embodiments, to generate a singular term distribution probability $P(t_n)$ for a term $t_n$, the NLP computing entity 106 performs operations corresponding to the equation:

$$P(t_n) = \frac{\sum_m \#(t_n, t_m)}{\sum_{p,q} \#(t_p, t_q)}, \quad \text{(Equation 1)}$$

where $\#(t_a, t_b)$ denotes a measure of frequency of co-occurrence of terms $t_a$ and $t_b$ in the preprocessed NLP data (e.g., occurrence of the two terms within the same digital document and/or within a threshold proximity of each other). In some embodiments, to generate a joint term distribution probability $P(t_n, t_m)$ for the terms $t_n$ and $t_m$, the NLP computing entity 106 performs operations corresponding to the equation:

$$P(t_n, t_m) = \frac{\#(t_m, t_n)}{\sum_{p,q} \#(t_p, t_q)}, \quad \text{(Equation 2)}$$

where $\#(t_a, t_b)$ denotes a measure of frequency of co-occurrence of terms $t_a$ and $t_b$ in the preprocessed NLP data.

At step/operation 905, the NLP computing entity 106 generates the term context correlation data for the selected terms based on the term occurrence probability data for the selected terms. In some embodiments, the term context correlation data include, for each pair of selected terms, a term correlation indicator. In some embodiments, the term correlation indicator for a pair of selected terms indicates a measure of co-occurrence frequency of the pair of selected terms in the NLP input data items 405. In some embodiments, the term correlation indicator for a pair of selected terms is determined based on a point-wise mutual information (PMI) indicator for the pair of selected terms. In some embodiments, to determine a term correlation indicator $r_{ij}$ for a pair of terms $t_i$ and $t_j$, the NLP computing entity 106 performs operations corresponding to the equation:

$$r_{ij} = PMI(t_i, t_j) = \max\left(\log \frac{P(t_i, t_j)}{P(t_i) P(t_j)}, 0\right). \quad \text{(Equation 3)}$$

At step/operation 705, the NLP computing entity 106 generates term-document correlation data for one or more selected terms and one or more digital documents associated with the NLP input data items 405, where the one or more selected terms may include at least some of the terms identified by the n-gram model. In some embodiments, the term-document correlation data may include a term-document correlation matrix that indicates, for each pair of a selected term and a digital document, an association measure for the pair based at least in part on an occurrence probability of the selected term in the digital document. In some embodiments, the term-document correlation data may include a term-document correlation matrix that indicates, for each pair of a selected term and a digital document, an association measure for the pair based at least in part on a predicted association of the selected term and the digital document.

Returning to FIG. 6, at step/operation 602, the NLP computing entity 106 (e.g., the user interaction unit 112 of the NLP computing entity 106) obtains user-defined term-topic correlation data (e.g., a user-defined term-topic correlation data matrix). In some embodiments, the user interaction unit 112 provides a topic model associated with the term-topic correlation data to an external computing entity 102 and in response receives the user-defined term-topic correlation data, which may include modifications to topic model associated with the term-topic correlation data. In some embodiments, the user interaction unit 112 generates the user-defined term-topic correlation data based at least in part on one or more topic modeling customization guidelines, based at least in part on one or more end user interactions with the NLP system 101, and/or based at least in part on one or more end user interactions with the NLP computing entity 106.

In some embodiments, the user-defined term-topic correlation data indicate, for each pair of a selected term and a selected topic, a measure of desired association between the selected term and the selected topic. In some embodiments, the user-defined term-topic definitions may include one or more of the following: (i) at least one request to modify a term-topic correlation indicator associated with the term-topic correlation data, (ii) at least one request to modify the term-topic correlation data by performing a merger of at least two topics associated with the initial term-topic correlation data, and (iii) at least one request to modify the term-topic correlation data by splitting a topic associated with the initial term-topic correlation data into at least two topics.

At step/operation 603, the NLP computing entity 106 (e.g., the topic-sentiment modeling unit 113 of the NLP computing entity 106) generates term-topic correlation data (e.g., a term-topic correlation matrix), document-sentiment correlation data (e.g., a document-sentiment correlation matrix), context-topic correlation data (e.g., a context-topic correlation matrix), and topic-sentiment correlation data (e.g., a topic-sentiment correlation matrix) based at least in part on the term-context correlation data (generated in step/operation 601), the term-document correlation data (generated in step/operation 601), the prior document sentiment values (generated in step/operation 601), and the user-defined term-topic definitions (obtained in step/operation 602). In some embodiments, the NLP computing entity 106 may perform at least a portion of the step/operation 603 using a factorization-based optimization, such as an NMF-based optimization.

In some embodiments, the context-topic correlation data indicate, for each topic and each semantic context characterized by co-occurrence of one or more terms and/or presence one or more text features, a context-topic correlation indicator that describes a predicted association between the semantic context and the topic. In some embodiments, the topic-sentiment correlation data indicate, for each topic, a predicted sentiment score. In some embodiments, the topic-sentiment correlation data indicate, for each topic and each sentiment label, a topic-sentiment correlation indicator that describes a predicted association between the topic and the sentiment label.

In some embodiments, to generate the term-topic correlation data U, the document-sentiment correlation data W, the context-topic correlation data $U_c$, and the topic-sentiment correlation data W based at least in part on the term-context correlation data R, the term-document correlation data W, the prior document sentiment values $W_0$, and the user-defined term-topic correlation data Y, the NLP computing entity performs operations that correspond to the below NMF-based optimization:

$$\min\left(\frac{1}{2}\right)\|R - UU_C^T\|^2 + \left(\frac{1}{2}\right)\|X - USW^T\|^2 + \left(\frac{1}{2}\right)\|(U-Y)M_u\|^2 + \left(\frac{1}{2}\mu\right) tr[(W-W_0)C(W-W_0)T], \quad \text{(Equation 4)}$$

where: (i) C is an adjustment matrix whose values may be pre-configured and/or pre-determined (e.g., based at least in part on configuration data in the storage subsystem 108 and/or one or more user inputs from an external computing entity), (ii) $M_U$ is a diagonal matrix for U-normalization, (iii) $\mu$ is a constant, such as a small positive constant value (e.g., $0<=\mu<=1$), whose value may be pre-configured and/or pre-determined (e.g., based at least in part on configuration data in the storage subsystem 108 and/or one or more user inputs from an external computing entity), (iv) tr indicates a matrix trace operation, and (v) T indicates a matrix transpose operation. Both U and $U_c$ are non-negative matrices. In some embodiments, each value for W is determined based at least in part on a constraint set. In some embodiments, each entry Cij of the adjustment matrix C is assigned a value of one if the sentiment values of the i-th row are known and is assigned a value of zero otherwise.

At step/operation 604, the NLP computing entity 106 (e.g., the user interaction unit 112 of the NLP computing entity 106) obtains the user-defined document-topic correlation data (e.g., a user-defined document-topic correlation matrix). In some embodiments, the user-defined document-topic correlation data may include one or more user-supplied topics for each digital document in at least a subgroup of the digital documents associated with the NLP input data items 405. For example, a user-defined topic-document correlation data may indicate that a first digital document is indicated by an end user profile to be related to billing.

At step/operation 605, the NLP computing entity (e.g., the topic-sentiment modeling unit 113 of the NLP computing entity 106) generates document-topic correlation data and document-sentiment correlation data based at least in part on the term-context correlation data (generated in step/operation 601), the term-topic correlation data (generated in step/operation 603), and the user-defined document-topic definitions (obtained in step/operation 604). In some embodiments, the NLP computing entity 106 may perform at least a portion of the step/operation 605 using a factorization-based optimization, such as an NMF-based optimization. For example, to generate the document-correlation data V and the document-sentiment correlation data W based at least in part on the term-document correlation data X, the term-topic correlation data U, and the user-defined document-topic correlation data Z, the NLP computing entity 106 may perform operations that correspond to the below NMF-based optimization:

$$\min\left(\frac{1}{2}\right)\|X - UV^T\|^2 + \left(\frac{1}{2}\right)\|M_V(V - Z)^T\|^2 \quad \text{(Equation 5)}$$

where: (i) $M_v$ is a diagonal matrix for V-normalization and (ii) T indicates a matrix transpose operation. In some embodiments, V is a nonzero matrix.

At step/operation 606, the NLP computing entity (e.g., the topic-sentiment modeling unit 113 of the NLP computing entity 106) generates the refined topic-sentiment detections 406. In some embodiments, the refined topic-sentiment detections 406 may include at least one of refined term-topic correlation data (e.g., a refined topic definition model), refined document-topic correlation data (e.g., a refined topic population model), refined topic labels for digital documents, refined topic quality metrics (e.g., topic coherence metrics), refined document-sentiment correlation data, and refined sentiment labels for digital documents.

In some embodiments, generating the refined topic-sentiment detections 406 may include processing the document-topic correlation data generated in step/operation 605 to generate a topic designation for each digital document associated with the NLP input data items 405. In some embodiments, generating the refined topic-sentiment detections 406 may include processing the document-sentiment correlation data generated in step/operation 605 to generate a sentiment value and/or a sentiment label for each digital document associated with unlabeled NLP input data items 402. For example, given an unlabeled digital document associated with medical feedback, the NLP computing entity 106 may process the document-topic correlation data and the document-sentiment correlation data for the unlabeled digital document to determine that the medical feedback contains a negative feedback and relates to inpatient services.

In some embodiments, generating the refined topic-sentiment detections may include using the term-topic correlation data obtained in step/operation 601 and the user-defined term-topic correlation data obtained in step/operation 602 to generate a topic model for the NLP input data items 405, where the topic model defines two or more topics each characterized by a distribution of term-topic correlation indicators for various terms (e.g., topic model 800 of FIG. 8). For example, given multiple digital documents associated with medical feedback, the NLP computing entity 106 may generate a topic model that defines a medical inpatient topic, a medical outpatient topic, and a post-release topic, where each of the noted topics are characterized by a distribution of term-topic correlation indicators for various terms. For example, the medical inpatient topic may be characterized by the following term-topic correlation indicators: 0.30 for the term "inpatient," 0.26 for the term "critical," 0.26 for the term "emergency," and/or the like (e.g., with the term-topic correlation indicators for various terms associated with each topic normalized such that they add up to one).

In some embodiments, generating the refined topic-sentiment detections may include generating topic quality metrics (e.g., topic coherence metrics) for a generated topic model. In some embodiments, to generate a topic coherence metric for a topic model, the NLP computing entity 106 aggregates (e.g., averages) topic-specific coherence metrics for each topic defined by the topic model. In some of those embodiments, to generate a topic-specific coherence metric for a particular topic defined by the topic model, the NLP computing entity 106 aggregates a measure of statistical deviation (e.g., a standard deviation and/or a variance) of term-topic correlation indicators associated with the particular topic. In some embodiments, the NLP computing entity 106 generates a topic-specific coherence metric for a particular topic defined by a topic model based on at least one of the following: (i) a measure of statistical deviation of term-topic correlation indicators associated with the particular topic, and (ii) a measure of statistical distribution (e.g., mean, median, or mode) of term-topic correlation indicators associated with the particular topic. In some embodiments, if the topic coherence metric for a topic model associated with particular NLP input data items falls below a threshold, the NLP computing entity 106 regenerates a topic model for the particular NLP input data items. Moreover, in some embodiments, the NLP computing entity 106 generates one or more topic designations (e.g., topic labels) for each topic defined by a generated topic model.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
   obtaining, by one or more processors, an initial term-topic correlation data object for a plurality of digital documents, wherein: (1) the initial term-topic correlation data object comprises a plurality of initial term-topic correlation indicators, and (2) the plurality of initial term-topic correlation indicators describes initial term-topic relationships between a plurality of terms and a plurality of initial topics;
   obtaining, by the one or more processors, a user-defined term-topic correlation data object for the plurality of digital documents, wherein: (1) the user-defined term-topic correlation data object comprises a plurality of user-defined term-topic correlation indicators, and (2) the plurality of user-defined term-topic correlation indicators describes user-defined term-topic relationships between the plurality of terms and one or more user-defined topics;
   generating, by the one or more processors, a refined term-topic correlation data object and a refined document-sentiment correlation data object for the plurality of digital documents based at least in part on the initial term-topic correlation data object and the user-defined term-topic correlation data object, wherein: (1) the refined term-topic correlation data object comprises a plurality of refined term-topic correlation indicators, (2) the plurality of refined term-topic correlation indicators describes refined term-topic relationships between the plurality of terms and the one or more user-defined topics, and (3) the refined document-sentiment correlation data object comprises a refined sentiment value for each digital document of the plurality of digital documents;
   obtaining, by the one or more processors, a user-defined document-topic correlation data object for the plurality of digital documents, wherein: (1) the user-defined document-topic correlation data object comprises a plurality of user-defined document-topic correlation indicators, and (2) the plurality of user-defined term-topic correlation indicators describes user-defined relationships between the plurality of digital documents and the one or more user-defined topics; and
   generating, by the one or more processors, a refined document-topic correlation object for the plurality of digital documents based at least in part on the refined term-topic correlation data object and the user-defined document-topic correlation data object, wherein: (1) the refined document-topic correlation data object comprises a plurality of refined document-topic correlation objects, and (2) the plurality of refined document-topic correlation indicators describes user-defined document-topic relationships between the plurality of digital documents and the one or more user-defined topics.

2. The computer-implemented method of claim 1, wherein:
   generating the refined term-topic correlation data object and the refined topic-sentiment correlation data object comprises performing a term-topic factorization-based optimization,
   the term-topic factorization-based optimization is associated with a plurality of term-topic factorization terms and one or more term-topic non-factorization terms,
   each term-topic factorization term of the plurality of term-topic factorization terms is associated with a term-topic factorized data object and a plurality of term-topic inferred data objects,
   the refined term-topic correlation data object is a term-topic inferred data object of the plurality of term-topic inferred data objects for a first term-topic factorization term of the plurality of term-topic factorization terms,
   the initial term-topic correlation data object is the term-topic factorized data object for a second term-topic factorization term of the plurality of term-topic factorization terms,
   the refined document-sentiment data object is associated with a first term-topic non-factorization term of the one or more term-topic non-factorization terms, and
   the user-defined term-topic correlation data object is associated with a second term-topic non-factorization term of the one or more term-topic non-factorization terms.

3. The computer-implemented method of claim 2, wherein:
   the term-topic factorization term for the first term-topic factorization term is a term context correlation data object for the plurality of digital documents, and
   the plurality of term-topic inferred terms for the first term-topic factorization term further comprise a transposed refined term-topic correlation data object.

4. The computer-implemented method of claim 2, wherein the plurality of term-topic inferred terms for the second term-topic factorization term comprise the refined term-topic correlation data object, a transposed refined document-sentiment data object, and a topic-sentiment correlation matrix.

5. The computer-implemented method of claim 2, wherein the first term-topic non-factorization term of the one or more term-topic non-factorization terms is further associated with a prior document sentiment value data object.

6. The computer-implemented method of claim 5, wherein:
the first term-topic non-factorization term of the one or more term-topic non-factorization terms is further associated with one or more first sentiment difference sub-terms, and
at least one of the one or more first sentiment difference sub-terms is associated with the refined document-sentiment correlation data object and the prior document sentiment score data object.

7. The computer-implemented method of claim 1, further comprising:
generating the user-defined term-topic correlation data object based at least in part on one or more user topic modeling inputs.

8. The computer-implemented method of claim 7, wherein:
the one or more user topic modeling inputs comprises a first user topic modeling input associated with a first user request to modify at least one selected initial term-topic correlation indicator of the plurality of initial term-topic indicators, and
generating the user-defined term-topic correlation data object comprises modifying each user-defined term-topic correlation indicator of the plurality of user-defined term-topic indicators that is associated with the at least one selected initial term-topic correlation indicator in accordance with the first user request.

9. The computer-implemented method of claim 7, wherein:
the one or more user topic modeling inputs comprises a second user topic modeling input associated with a second user request to merge two or more pre-merge topics of the plurality of initial topics into a merged topic of the one or more user-defined topics,
generating the user-defined term-topic correlation data object comprises generating one or more merged term-topic correlation indicators of the plurality of user-defined term-topic correlation indicators,
each merged topic-topic correlation indicator of the plurality of user-defined term-topic correlation indicators is determined based at least in part on two or more pre-merge term-topic correlation indicators of the plurality of initial term-topic correlation indicators, and
each pre-merge term-topic correlation indicator of the two or more pre-merge term-topic correlation indicators is associated with a respective pre-merge topic of the two or more pre-merge topics.

10. The computer-implemented method of claim 7, wherein:
the one or more user topic modeling inputs comprises a third user topic modeling input associated with a third user request to split a pre-split topic of the plurality of initial topics into two or more post-split topics of the one or more user-defined topics,
the pre-split topic is associated with one or more pre-split term-topic correlation indicators of the plurality of initial term-topic correlation indicators,
each post-split topic of the two or post-split topics is associated with a respective pre-split portion of the one or more pre-split term-topic correlation indicators,
each post-split topic of the two or post-split topics is associated with a respective post-split portion of the plurality of user-defined term-topic correlation indicators, and
each respective post-split portion for a post-split topic of the two or post-split topics is determined based at least in part on the respective pre-split portion for the post-split topic.

11. The computer-implemented method of claim 7, wherein:
generating the refined document-topic correlation data object comprises performing a document-topic factorization-based optimization,
the document-topic factorization-based optimization is associated with one or more document-topic factorization terms,
each document-topic factorization term of the one or more document-topic non-factorization terms is associated with a document-topic factorized data object and a plurality of document-topic inferred data objects, and
a transposed refined document-topic correlation data object that is associated with the refined document-topic correlation data object is a document-topic inferred data object of the plurality of document-topic inferred data objects for a first document-topic factorization term of the one or more document-topic non-factorization terms.

12. The computer-implemented method of claim 1, wherein the plurality of digital documents comprise one or more medical feedback documents.

13. An apparatus comprising at least one processor and at least one non-transitory memory comprising program code, wherein the at least one non-transitory memory and the program code are configured to, with the at least one processor, cause the apparatus to:
obtain an initial term-topic correlation data object for a plurality of digital documents, wherein: (1) the initial term-topic correlation data object comprises a plurality of initial term-topic correlation indicators, and (2) the plurality of initial term-topic correlation indicators describes initial term-topic relationships between a plurality of terms and a plurality of initial topics;
obtain a user-defined term-topic correlation data object for the plurality of digital documents, wherein: (1) the user-defined term-topic correlation data object comprises a plurality of user-defined term-topic correlation indicators, and (2) the plurality of user-defined term-topic correlation indicators describes user-defined term-topic relationships between the plurality of terms and one or more user-defined topics;
generate a refined term-topic correlation data object and a refined document-sentiment correlation data object for the plurality of digital documents based at least in part on the initial term-topic correlation data object and the user-defined term-topic correlation data object, wherein: (1) the refined term-topic correlation data object comprises a plurality of refined term-topic correlation indicators, (2) the plurality of refined term-topic correlation indicators describes refined term-topic relationships between the plurality of terms and the one or more user-defined topics, and (3) the refined document-sentiment correlation data object comprises a refined sentiment value for each digital document of the plurality of digital documents;
obtain a user-defined document-topic correlation data object for the plurality of digital documents, wherein: (1) the user-defined document-topic correlation data object comprises a plurality of user-defined document-topic correlation indicators, and (2) the plurality of user-defined term-topic correlation indicators describes user-defined relationships between the plurality of digital documents and the one or more user-defined topics; and generate a refined document-topic correlation object for the plurality of digital documents based at least in part on the refined term-topic correlation data object and the user-defined document-topic correlation data object, wherein: (1) the refined document-topic correlation data object comprises a plurality of refined document-topic correlation objects, and (2) the plurality of refined document-topic correlation indicators describes user-defined document-topic relationships between the plurality of digital documents and the one or more user-defined topics.

14. The apparatus of claim 13, wherein:
generating the refined term-topic correlation data object and the refined topic-sentiment correlation data object comprises performing a term-topic factorization-based optimization,
the term-topic factorization-based optimization is associated with a plurality of term-topic factorization terms and one or more term-topic non-factorization terms,
each term-topic factorization term of the plurality of term-topic factorization terms is associated with a term-topic factorized data object and a plurality of term-topic inferred data objects,
the refined term-topic correlation data object is a term-topic inferred data object of the plurality of term-topic inferred data objects for a first term-topic factorization term of the plurality of term-topic factorization terms,
the initial term-topic correlation data object is the term-topic factorized data object for a second term-topic factorization term of the plurality of term-topic factorization terms,
the refined document-sentiment data object is associated with a first term-topic non-factorization term of the one or more term-topic non-factorization terms, and
the user-defined term-topic correlation data object is associated with a second term-topic non-factorization term of the one or more term-topic non-factorization terms.

15. The apparatus of claim 14, wherein:
the term-topic factorization term for the first term-topic factorization term is a term context correlation data object for the plurality of digital documents, and
the plurality of term-topic inferred terms for the first term-topic factorization term further comprise a transposed refined term-topic correlation data object.

16. The apparatus of claim 14, wherein the plurality of term-topic inferred terms for the second term-topic factorization term comprise the refined term-topic correlation data object, a transposed refined document-sentiment data object, and a topic-sentiment correlation matrix.

17. A non-transitory computer storage medium comprising instructions configured to cause one or more processors to at least at least perform:
obtain an initial term-topic correlation data object for a plurality of digital documents, wherein: (1) the initial term-topic correlation data object comprises a plurality of initial term-topic correlation indicators, and (2) the plurality of initial term-topic correlation indicators describe initial term-topic relationships between a plurality of terms and a plurality of initial topics;

obtain a user-defined term-topic correlation data object for the plurality of digital documents, wherein: (1) the user-defined term-topic correlation data object comprises a plurality of user-defined term-topic correlation indicators, and (2) the plurality of user-defined term-topic correlation indicators describes user-defined term-topic relationships between the plurality of terms and one or more user-defined topics;

generate a refined term-topic correlation data object and a refined document-sentiment correlation data object for the plurality of digital documents based at least in part on the initial term-topic correlation data object and the user-defined term-topic correlation data object, wherein: (1) the refined term-topic correlation data object comprises a plurality of refined term-topic correlation indicators, (2) the plurality of refined term-topic correlation indicators describes refined term-topic relationships between the plurality of terms and the one or more user-defined topics, and (3) the refined document-sentiment correlation data object comprises a refined sentiment value for each digital document of the plurality of digital documents;

obtain a user-defined document-topic correlation data object for the plurality of digital documents, wherein: (1) the user-defined document-topic correlation data object comprises a plurality of user-defined document-topic correlation indicators, and (2) the plurality of user-defined term-topic correlation indicators describes user-defined relationships between the plurality of digital documents and the one or more user-defined topics; and generate a refined document-topic correlation object for the plurality of digital documents based at least in part on the refined term-topic correlation data object and the user-defined document-topic correlation data object, wherein: (1) the refined document-topic correlation data object comprises a plurality of refined document-topic correlation objects, and (2) the plurality of refined document-topic correlation indicators describes user-defined document-topic relationships between the plurality of digital documents and the one or more user-defined topics.

18. The non-transitory computer storage medium of claim 17, wherein:
generating the refined term-topic correlation data object and the refined topic-sentiment correlation data object comprises performing a term-topic factorization-based optimization,
the term-topic factorization-based optimization is associated with a plurality of term-topic factorization terms and one or more term-topic non-factorization terms,
each term-topic factorization term of the plurality of term-topic factorization terms is associated with a term-topic factorized data object and a plurality of term-topic inferred data objects,
the refined term-topic correlation data object is a term-topic inferred data object of the plurality of term-topic inferred data objects for a first term-topic factorization term of the plurality of term-topic factorization terms,
the initial term-topic correlation data object is the term-topic factorized data object for a second term-topic factorization term of the plurality of term-topic factorization terms,
the refined document-sentiment data object is associated with a first term-topic non-factorization term of the one or more term-topic non-factorization terms, and the user-defined term-topic correlation data object is associated with a second term-topic non-factorization term of the one or more term-topic non-factorization terms.

19. The non-transitory computer storage medium of claim 18, wherein:
the term-topic factorization term for the first term-topic factorization term is a term context correlation data object for the plurality of digital documents, and
the plurality of term-topic inferred terms for the first term-topic factorization term further comprise a transposed refined term-topic correlation data object.

20. The non-transitory computer storage medium of claim 18, wherein the plurality of term-topic inferred terms for the second term-topic factorization term comprise the refined term-topic correlation data object, a transposed refined document-sentiment data object, and a topic-sentiment correlation matrix.

* * * * *

UNITED STATES PATENT AND TRADEMARK OFFICE
CERTIFICATE OF CORRECTION

Page 1 of 1

PATENT NO. : 11,238,243 B2
APPLICATION NO. : 16/585201
DATED : February 1, 2022
INVENTOR(S) : Roy et al.

It is certified that error appears in the above-identified patent and that said Letters Patent is hereby corrected as shown below:

In the Claims

Column 27
Line 40, "obtaining" should read --receiving--
Line 48, "obtaining" should read --receiving--

Column 28
Line 5, "obtaining" should read --receiving--

Column 30
Line 36, "obtain" should read --receive--
Line 43, "obtain" should read --receive--
Line 65, "obtain" should read --receive--

Column 31
Line 59, "to at least at least perform" should read --to at least perform--
Line 60, "obtain" should read --receive--

Column 32
Line 1, "obtain" should read --receive--
Line 23, "obtain" should read --receive--

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*